US008551554B2

(12) United States Patent
Liu

(10) Patent No.: US 8,551,554 B2
(45) Date of Patent: Oct. 8, 2013

(54) APPLE PEEL POWDER, METHODS OF MAKING, AND USES THEREOF

(75) Inventor: Rui Hai Liu, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1047 days.

(21) Appl. No.: 11/018,833

(22) Filed: Dec. 20, 2004

(65) Prior Publication Data
US 2005/0147723 A1 Jul. 7, 2005

Related U.S. Application Data

(60) Provisional application No. 60/532,992, filed on Dec. 29, 2003.

(51) Int. Cl.
*A23B 7/00* (2006.01)

(52) U.S. Cl.
USPC .......................................... 426/640; 426/615

(58) Field of Classification Search
USPC .................................................. 426/615, 640
See application file for complete search history.

(56) References Cited

U.S. PATENT DOCUMENTS

| | | | |
|---|---|---|---|
| 4,267,196 A | 5/1981 | Johnston | |
| 4,514,428 A | 4/1985 | Glass et al. | |
| 4,647,469 A * | 3/1987 | Jakobsson et al. | 426/524 |
| 5,994,413 A | 11/1999 | Tanabe et al. | |
| 6,268,012 B1 * | 7/2001 | Sikora et al. | 426/640 |
| 6,506,421 B2 | 1/2003 | Paufique | |
| 6,509,054 B1 * | 1/2003 | Haddad et al. | 426/615 |
| 6,620,452 B1 | 9/2003 | Haddad et al. | |
| 6,638,542 B2 | 10/2003 | Nieuwenhuizen et al. | |
| 6,642,277 B1 | 11/2003 | Howard et al. | |
| 2002/0004080 A1 | 1/2002 | Paufique | |
| 2003/0059515 A1 | 3/2003 | Haddad et al. | |
| 2004/0014805 A1 | 1/2004 | Shoji | |

FOREIGN PATENT DOCUMENTS

| CN | 1307830 A | * | 8/2001 |
|---|---|---|---|
| SU | 1526628 A | * | 12/1989 |

OTHER PUBLICATIONS

Wolfe et al. "Apple peels as a value added food ingredient", J. Agri. Food Chem, 2003, 51, 1676-1683, pp. 8.*
Masoodi et al "Use of Apple Pomace powder as a source of dietary fiber in wheat bread", J of Food Processing and Preservation 22 (1998) 255-263.*
Wolfe et al. "Apple peels are Rich in Phytochemicals and Have High Antioxidant Activity", New York Fruit Quarterly vol. 10, No. 3, Fall 2002, pp. 1 and 9-11.*
Arts et al., "Catechin Contents of Foods Commonly Consumed in The Netherlands. 1. Fruits, Vegetables, Staple Foods, and Processed Foods," *J. Agric. Food Chem.* 48:1746-1751 (2000).
Awad et al., "Flavonoid and Chlorogenic Acid Concentrations in Skin of 'Jonagold' and 'Elstar' Apples During and After Regular and Ultra Low Oxygen Storage," *Postharvest Biol. Technol.* 20:15-24 (2000).
Awad et al., "Flavonoid and Chlorogenic Acid Levels in Apple Fruit: Characterisation of Variation," *Sci. Hortic.* 83:249-263 (2000).
Awad et al., "Effects of Light on Flavonoid and Chlorogenic Acid Levels in the Skin of 'Jonegold' Apples," *Sci. Hortic.* 88:289-298 (2001).
Bomben et al., "Converting an Uneconomical By-product Into a Useful Product," *Food Technol.* 25:1108-1117 (1971).
Boyles et al., "Anthocyanin Composition of Red Raspberry Juice: Influences of Cultivar, Processing, and Environmental Factors," *J. Food Sci.* 58:1135-1141 (1993).
Burda et al., "Phenolic Compounds and Their Changes in Apples During Maturation and Cold Storage," *J. Agric. Food Chem.* 38:945-948 (1990).
Delgado-Vargas et al., "Natural Pigments: Carotenoids, Anthocyanins, and Betalains—Characteristics, Biosynthesis, Processing, and Stability," *Crit. Rev. Food Sci. Nutr.* 40:173-289 (2000).
Dewanto et al., "Thermal Processing Enhances the Nutritional Value of Tomatoes by Increasing Total Antioxidant Activity," *J. Agric. Food Chem.* 50:3010-3014 (2002).
Dewanto et al., "Processed Sweet Corn Has Higher Antioxidant Activity," *J. Agric. Food Chem.* 50:4959-4964 (2002).
Doll and Peto, "The Causes of Cancer: Quantitative Estimates of Avoidable Risks of Cancer in the United States Today," *J. Natl. Cancer Inst.* 66:1192-1308 (1981).
Dragsted et al., "Cancer-Protective Factors in Fruits and Vegetables: Biochemical and Biological Background," *Pharmacol. Toxicol.* 72:116-135 (1993).
Eberhardt et al., "Antioxidant Activity of Fresh Apples," *Nature* 405:903-904 (2000).
Escarpa & González, "High-Performance Liquid Chromatographt with Diode-Array Detection for the Determination of Phenolic Compounds in Peel and Pulp from Different Apple Varieties," *J. Chromatogr.* 823:331-337 (1998).
Ewald et al., "Effect of Processing on Major Flavonoids in Processed Onions, Green Beans, and Peas," *Food Chem.* 64:231-235 (1999).
Gil et al., "Antioxidant Activity of Pomegranate Juice and Its Relationship with Phenolic Composition and Processing," *J. Agric. Food Chem.* 48:4581-4589 (2000).
Gillman et al., "Protective Effect of Fruits and Vegetables on Development of Stroke in Men," *J. Am. Med. Assoc.* 273:1113-1117 (1995).

(Continued)

Primary Examiner — Jyoti Chawla
(74) *Attorney, Agent, or Firm* — LeClairRyan, a Professional Corporation

(57) ABSTRACT

The present invention relates to a method of making a powder from apple peel by providing an apple peel, subjecting the apple peel to a phytochemical preservation treatment, drying the treated apple peel, and grinding the dried, treated apple peel to a powder. A powder from apple peel having a phenolic content and a flavonoid content similar to fresh apple peel on a fresh weight basis, where the powder has a water activity of less than 0.30 is also disclosed. The present invention also relates to a method of treating cancer in a patient by administering a powder from apple peel to a patient under conditions effective to treat cancer. Also disclosed is a method of inhibiting proliferation of cancer cells by contacting cancer cells with a powder from apple peel under conditions effective to inhibit proliferation of the cancer cells.

9 Claims, 14 Drawing Sheets

(56) References Cited

OTHER PUBLICATIONS

Golding et al., "Fate of Apple Peel Phenolics During Cool Storage," *J. Agric. Food Chem.* 49:2283-2289 (2001).
Goodrich et al., "Glucosinolate Changes in Blanched Broccoli and Brussels Sprouts," *J. Food Proc. Preserv.* 13:275-280 (1989).
Hertog et al. "Intake of Potentially Anticarcinogenic Flavinoids and Their Determinants in Adults in The Netherlands," *Nutr. Cancer* 20(1):21-29 (1993).
Hertog et al., "Dietary Antioxidant Flavinoids and Risk of Coronary Heart Disease: The Zutphen Elderly Study," *Lancet* 342:1007-1011 (1993).
Hirota et al., "Tissue and Spatial Distribution of Flavonol and Peroxidase in Onion Bulbs and Stability of Flavonol Glucosides During Boiling of the Scales," *J. Agric. Food Chem.* 46:3497-3502 (1998).
Joshipura et al., "The Effect of Fruit and Vegetable Intake on Risk for Coronary Heart Disease" *Ann. Intern. Med.* 134:1106-1114 (2001).
Ju et al., "Relationships Among Simple Phenol, Flavonoid and Anthocyanin in Apple Fruit Peel at Harvest and Scald Susceptibility," *Postharvest Biol. Technol.* 8:83-93 (1996).
Knekt et al., "Dietary Flavonoids and the Risk of Lung Cancer and Other Malignant Neoplasms," *Am. J. Epidemiol.* 146:223-230 (1997).
Knekt et al., "Flavonoid Intake and Coronary Mortality in Finland: A Cohort Study," *Brit. Med. J.* 312:478-481 (1996).
Knekt et al., "Quercetin Intake and the Incidence of Cerebrovascular Disease," *Eur. J. Clin. Nutr.* 54:415-417 (2000).
Le Marchand et al., "Intake of Flavonoids and Lung Cancer," *J. Natl. Cancer Inst.* 92:154-160 (2000).
Lister et al., "Development Changes in the Concentration and Composition of Flavonoids in Skin of Red and Green Apple Cultivar,"*J. Sci. Food Agric.* 64:155-161 (1994).
Liu et al., "Antioxidant and Antiprolifereative Activities of Raspberries," *J. Agric. Food Chem.* 50:2926-2930 (2002).
Liu et al., "Effects of Tumor Necrosis Factor Alpha on the Expression of Connective Tissue Growth Factor in Hepatic Stellate Cells," *Zhonghua Gan Zang Bing Za Zhi (N. Y. Fruit Q.)* 9 Suppl:15-17 (2001).
Podsedek et al., "Antioxidative Capacity of Tomato Products," *Eur. Food Res. Technol.* 210:268-272 (2000).
Shewfelt, R.L., "Flavor and Color of Fruits as Affected by Processing," *in* Commercial Fruit Processing, Woodroof and Luh, Eds., AVI Publishing Company, Inc.: Westport, pp. 481-529 (1986).
Singleton et al., "Analysis of Total Phenols and Other Oxidation Substrates and Antioxidants by Means of Folin-Ciocalteu Reagent," *Methods Enzymol.* 299:152-178 (1999).
Tabak et al., "Chronic Obstructive Pulmonary Disease and Intake of Catechins, Flavonols, and Flavones," *Am. J. Respir. Crit. Care Med.* 164:61-64 (2001).
Talcott et al., "Antioxidant Changes and Sensory Properties of Carrot Puree Processed With and Without Periderm Tissue," *J. Agric. Food Chem.* 48:1315-1321 (2000).
Talcott et al., "Contribution of Periderm Material and Blanching Time to the Quality of Pasteurized Peach Puree," *J. Agric. Food Chem.* 48:4590-4596 (2000).
Van Der Sluis et al., "Activity and Concentration of Polyphenolic Antioxidants in Apple: Effect of Cultivar, Harvest Year, and Storage Conditions," *J. Agri. Food Chem.* 49:3606-3613 (2001).
Vinson et al., "Phenol Antioxidant Quantity and Quality in Food:Fruits," *J. Agric. Food Chem.* 49:5315-5321 (2001).
Wang et al., "Total Antioxidant Capacity of Fruits," *J. Agric. Food Chem.* 44:701-705 (1996).
Willett, W.C., "Diet, Nutrition, and Avoidable Cancer," *Environ. Health Perspect.* 103:165-170 (1995).
Winston et al., "A Rapid Gas Chromatographic Assay for Determining Oxyradical Scavenging Capacity of Antioxidants and Biological Fluids," *Free Rad. Biol. Med.* 24:480-493 (1998).
Yamanashi et al., "Relationship Between Change of Fresh-Roasted Flavor and Titratable Acidity of Stored Ground Coffee," *Nippon Shokuhin Kogyo Gakkaishi* 39:88-92 (1992).
Zhishen et al., "The Determination of Flavonoid Contents in Mulberry and Their Scavenging Effects on Superoxide Radicals," *Food Chem.* 64:555-599 (1999).
Brown et al., "Uptake of Quercetin and Quercetin 3-Glucoside from Whole Onion and Apple Peel Extracts by Caco-2 Cell Monolayers," J. Agric. Food Chem. 52(23):7172-7179 (2004) (abstract only).
Bendini et al., "Radical Scavenging Activities of Peels and Pulps from cv. Golden Delicious Apples as Related to their Phenolic Composition," J. Agric. Food Chem. 52(15):4684-4689 (2004) (abstract only).
Ding et al., "Inhibition of AP-1 and Neoplastic Transformation by Fresh Apple Peel Extract," J. Biol. Chem. 279 (11):10670-10676 (2004) (abstract only).
Leontowicz et al., "Apple and Pear Peel and Pulp and their Influence on Plasma Lipids and Antioxidant Potentials in Rats Fed Cholesterol-Containing Diets," J. Agric. Food Chem. 51(19):5780-5785 (2003) (abstract only).
Lee et al., "Major Phenolics in Apple and Their Contribution to the Total Antioxidant Capacity," J. Agric. Food Chem. 51(22):6516-6520 (2003) (abstract only).
"Worldwide Gourmet," http://groumet.sympatico.ca/fruits/apple/medicinal.htm, 2002.
Wolfe et al., "Antioxidant Activity of Apple Peels," J. Agric. Food Chem. 51(3):609-614 (2003) (abstract only).
Lommen et al., "Application of Directly Coupled HPLC-NMR-MS to the Identification and Confirmation of Quercetin Glycosides and Phloretin Glycosides in Apple Peel," Anal. Chem. 72(8):1793-1797 (2000) (abstract only).
Kahkonen et al., "Antioxidant Activity of Plant Extracts Containing Phenolic Compounds," J. Agric. Food Chem. 47 (10):3954-3962 (1999) (abstract only).
"Health Sciences Group Acquires Apple Peel Technologies," http://uk.us.biz.yahoo.com/bw/041129/295661_1.html, Nov. 29, 2004.
"Apple Peel Powder," http://ift.confex.com/ift/2003/techprogram/paper_17557.htm, Jul. 2003.

* cited by examiner

40°C　　　60°C　　　80°C　　　Air-dried　　　Freeze-dried

APPLE PEEL POWDER, METHODS OF MAKING, AND USES THEREOF

This application claims the benefit of U.S. Provisional Patent Application Ser. No. 60/532,992, filed Dec. 29, 2003.

FIELD OF THE INVENTION

This invention relates to apple peel powder, methods of making apple peel powder, and uses thereof.

BACKGROUND OF THE INVENTION

The leading causes of death in the U.S. are cardiovascular diseases and cancer. Both types of diseases are thought to be partially the result of oxidative stress, which can lead to damage of biomolecules. It has been hypothesized that an increase in dietary antioxidants can reduce oxidative stress and prevent chronic diseases. Doll and Peto (*J. Natl. Cancer Inst.* 66:1192-1308 (1981)), estimated that 35% (range 10-70%) of deaths from cancer could be avoided by dietary modifications. Willett (*Environ. Health Perspect.* 103:165-170 (1995)) later narrowed the range to 20-42%, stating that roughly 32% of cancers could be prevented by changes in diet. Fruits and vegetables contain many compounds, including phenolics, thiols, carotenoids, tocopherols, and glucosinolates, that may exert chemoprotective effects through a variety of mechanisms (Dragsted et al., *Pharmacol. Toxicol.* 72:116-135 (1993)). Increased intake of fruits and vegetables has also been associated with reduced risk of coronary heart disease (CHD) (Joshipura et al., *Ann. Intern. Med.* 134:1106-1114 (2001)) and stroke (Gillman et al., *J. Am. Med. Assoc.* 273:1113-1117 (1995)). Flavonoids, commonly found in fruits and vegetables, have been linked to reduced risk or mortality from CHD (Hertog et al., *Lancet* 342:1007-1011 (1993)). Such findings have lead the National Research Council (NRC) to recommend consuming five or more servings of fruits and vegetables a day.

Apples are a very significant part of the diet. From a Dutch Food Consumption Survey and previously analyzed flavonoid contents of fruits, vegetables, and beverages, Hertog et al. (*Nutr. Cancer* 20:21-29 (1993)) determined that apples are the third largest contributors of flavonoids in the Dutch diet behind tea and onions. In Finland, along with onions, apples are the top contributors (Knekt et al., *Am. J. Epidemiol.* 146:223-230 (1997)). Twenty-two percent of the fruit phenolics consumed in the U.S. are from apples, making them the largest source (Vinson et al., *J. Agric. Food Chem.* 49:5315-5321 (2001)). Consumption of apples has been linked to the prevention of chronic disease. Apple intake has been negatively associated with lung cancer incidence in two separate studies (Knekt et al., *Am. J. Epidemiol.* 146:223-230 (1997); Le Marchand et al., *J. Natl. Cancer Inst.* 92:154-160 (2000)). It has also been related to reduced cardiovascular disease. Coronary and total mortality (Knekt et al., *Brit. Med. J.* 312: 478-481 (1996)), symptoms of chronic obstructive pulmonary disease (Tabak et al., *Am. J. Respir. Crit. Care Med.* 164:61-64 (2001)), and risk of thrombotic stroke (Knekt et al., *Eur. J. Clin. Nutr.* 54:415-417 (2000)) have all been inversely associated with apple consumption.

Apples are a good source of phenolic compounds (Eberhardt et al., *Nature* 405:903-904 (2000)). The total extractable phenolic content has been investigated and ranges from 110-357 mg/100 g fresh apple (Podsedek et al., *Eur. Food Res. Technol.* 210:268-272 (2000); Liu et al., *N.Y. Fruit Q.* 9:15-17 (2001)). It is known that the concentration of total phenolic compounds is much greater in the peel of apples than in the flesh (Burda et al., *J. Agric. Food Chem.* 38:945-948 (1990); Ju et al., *Postharvest Biol. Technol.* 8:83-93 (1996); Escarpa et al., *J. Chromatogr.* 823:331-337 (1998)). The nature and distribution of these phytochemicals between the flesh and the peel of the apple is also different. For example, while the fleshy part of the apple contains catechins, procyanidins, phloridzin, phloretin glycosides, caffeic acid and chlorogenic acid, the apple peel possesses all of these compounds and has additional flavonoids not found in the flesh, such as quercetin glycosides and cyanidin glycosides (Burda et al., *J. Agric. Food Chem.* 38:945-948 (1990); Escarpa et al., *J. Chromatogr.* 823:331-337 (1998); Golding et al., *J. Agri. Food Chem.* 49:2283-2289 (2001); van der Sluis et al., *J. Agri. Food Chem.* 49:3606-3613 (2001)). It has been noted in other fruits and vegetables that the peels have high phytochemical concentrations and/or high antioxidant activity (Talcott et al., *J. Agric. Food Chem.* 48:4590-4596 (2000); Gil et al., *J. Agric. Food Chem.* 48:4581-4589 (2000); Talcott et al., *J. Agric. Food Chem.* 48:1315-1321 (2000); Ewald et al., *Food Chem.* 64:231-235 (1999); Mizuno et al., *Nippon Shokuhin Kogyo Gakkaishi* 39:88-92 (1992); Hirota et al., *J. Agric. Food Chem.* 46:3497-3502 (1998)).

Peeled and unpeeled apples have high antioxidant activity and inhibit the growth of human cancer cells in vitro (Eberhardt et al., *Nature* 405:903-904 (2000)). The antioxidant and antiproliferative activities of unpeeled apples is greater than that of peeled apples (Eberhardt et al., *Nature* 405:903-904 (2000)). Apple peels are a waste product of applesauce and canned apple manufacture. Industrially, apples are peeled both by using a hot caustic method and mechanically. The National Agriculture Statistics Service (NASS) (USDA, *National Agriculture Statistics Service*, 2002) reported that 267 million pounds of apples were processed in applesauce and canned apple production in New York State alone in 2001. The apple peels are typically used for non-valuable purposes. For instance, the peels, along with the core materials of the apples, are often pressed to make juice or vinegar, pressed into a cake for livestock feed, or used as fertilizer. Sometimes apple peels and core materials are used as a source of pectin.

An attempt was made in the past to create a valuable product from apple peels (Bomben et al., *Food Technol.* 25:1108-1117 (1971)). The peels from apples were soaked, macerated and mixed with macerated core materials that had been deseeded and destemmed. The mixture was then drum-dried and passed through a 100-mesh screen. The powder was used as a thickener in apple pies. The harsh drying conditions resulted in the loss of most of the aroma from the peels and a brown appearance. The pies made with the apple peel powder did not have higher taste ratings, probably due to the undesirable brown color of the powder.

The need thus remains to find a valuable use of the millions of pounds of waste peels generated from applesauce and canned apple processing each year in this country.

SUMMARY OF THE INVENTION

One aspect of the present invention relates to a method of making a powder from apple peel. This method involves providing an apple peel, subjecting the apple peel to a phytochemical preservation treatment, drying the treated apple peel, and grinding the dried, treated apple peel to a powder.

Another aspect of the present invention relates to a powder from apple peel having a phenolic content and a flavonoid content similar to fresh apple peel on a fresh weight basis, where the powder has a water activity of less than 0.30.

Another aspect of the present invention relates to a method of treating cancer in a patient. This method involves administering a powder from apple peel to a patient under conditions effective to treat cancer.

Still another aspect of the present invention relates to a method of inhibiting proliferation of cancer cells. This method involves contacting cancer cells with a powder from apple peel under conditions effective to inhibit proliferation of the cancer cells.

DETAILED DESCRIPTION OF THE INVENTION

Figure 1:
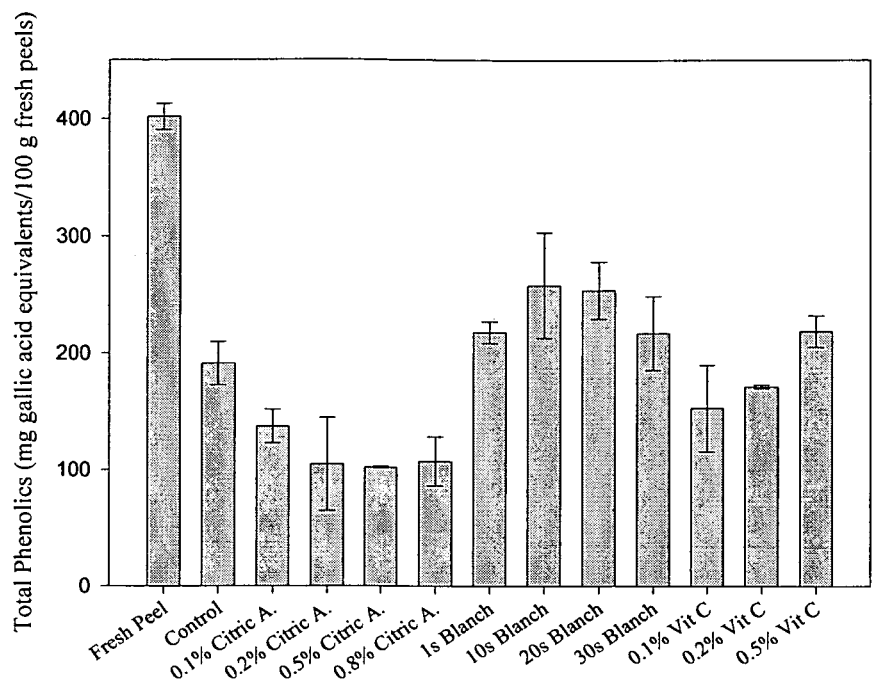
FIG. 1 is a graph showing total phenolic content of treated Rome Beauty apple peels oven-dried at 60° C. (mean±SD, n=3).

The present invention relates to a method of making a powder from apple peel. This method involves providing an apple peel, subjecting the apple peel to a phytochemical preservation treatment, drying the treated apple peel, and grinding the dried, treated apple peel to a powder.

In carrying out the methods of the present invention, apple peel may be provided from all varieties of apples. Preferably, the apple variety is Idared, Rome Beauty, Cortland, or Golden Delicious. Most preferably, the apple variety is Idared or Rome Beauty. Apple peel is the outer portion of the apple, which is removed by an apple parer, or by any other means.

Once an apple peel is provided, it is subjected to a phytochemical preservation treatment. The phytochemical preservation treatment preserves the phytochemical content of the apple peel, thus optimizing phytochemical content of the resulting apple peel powder. Suitable phytochemical preservation treatments include, but are not limited to, a citric acid dip, an ascorbic acid dip, a boiling water dip, or combinations thereof.

In one embodiment, the apple peel is dipped in a 0.05 to 1.0% acidic solution. Suitable acids include citric acid or ascorbic acid. After such dipping, the apple peel is drained.

Alternatively, the apple peel is blanched in boiling water. After blanching, the apple peel is dipped in a bath of cool water. In some instances, the apple peel is treated with ascorbic acid following a bath of cool water.

Following the phytochemical preservation treatment, the treated apple peel is dried. Suitable methods of drying the treated apple peel include, but are not limited to, oven-drying, air-drying, and freeze-drying. Preferably, the treated apple peel is freeze-dried.

In accordance with the methods of the present invention, treated, dried apple peel is then ground to a powder. Preferably, the apple peel is ground under conditions effective to produce a 40-60 mesh powder.

Another aspect of the present invention relates to a powder from apple peel having a phenolic content and a flavonoid content similar to fresh apple peel on a fresh weight basis, where the powder has a water activity of less than 0.30.

One of the unique features of the apple peel powder of the present invention is the presence of phytochemicals, such as phenolics, flavonoids, and anthocyanins. Preferably, the apple peel powder comprises phenolics in a concentration of about 350-650 mg gallic acid equivalents per 100 grams of fresh apple peel, flavonoids in a concentration of about 250-450 mg catechin equivalents per 100 grams of fresh apple peel, and anthocyanins in a concentration of about 1-50 mg cyanidin 3-glucoside equivalents per 100 grams of fresh apple peel.

Preferably, the apple peel powder of the present invention has an antioxidant activity of about 200-300 μmol vitamin C equivalents per 1 gram of fresh apple peel. In addition, the apple peel powder preferably has antiproliferative activity with a median effective dose $EC_{50}$ of about 9-15 mg fresh apple peel/mL.

The phenolic content, flavonoid content, antioxidant activity, and/or antiproliferative activity of the apple peel powder of the present invention is similar to the phenolic content, flavonoid content, antioxidant activity, and/or antiproliferative activity, respectively, of fresh apple peel on a fresh weight basis. In other words, when fully rehydrated, the apple peel powder of the present invention is similar to fresh apple peel with regard to phytochemical characteristics.

In addition to powder from apple peels, powder may also be obtained from other fruit peels, such as from grape peel and cranberry peel using the method of the present invention.

The apple peel powder of the present invention is suitable as a dietary supplement. In one embodiment, the apple peel powder is incorporated into a capsule. In another embodiment, the apple peel powder is incorporated into a compressed tablet. In yet another embodiment, the apple peel powder is added to a foodstuff. The apple peel powder may be added to any foodstuff, such as sauce, tea, candy, cereals, breads, fruit mixes, fruit salads, salads, snack bars, fruit leather, health bars, granola, smoothies, soups, juices, cakes, pies, shakes, ice cream, and health drinks.

Another aspect of the present invention relates to a method of treating cancer in a patient. This method involves administering a powder from apple peel to a patient under conditions effective to treat cancer.

The apple peel powder of the present invention is preferably administered in a single unit dosage form that contains an amount of apple peel powder effective to treat cancer. The apple peel powder can also include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent apple peel powder.

The apple peel powder, when combined with any suitable excipients or stabilizers, and whether administered alone or in the form of a composition, can be administered orally. For most therapeutic purposes, the apple peel powder can be administered orally as a solid or as a solution or suspension in liquid form.

The solid unit dosage forms of the apple peel powder can be of a conventional type. The solid form can be a capsule, such as an ordinary gelatin type containing the apple peel powder and a carrier, for example, lubricants and inert fillers such as, lactose, sucrose, or cornstarch. In another embodiment, the apple peel powder is tableted with conventional tablet bases such as lactose, sucrose, or cornstarch in combination with binders like acacia or gelatin, disintegrating agents such as cornstarch, potato starch, or alginic acid, and a lubricant such as stearic acid or magnesium stearate.

The apple peel powder may be administered in combination with other therapeutic regimens that are known in the art, whether now known or hereafter developed.

In yet another aspect of the present invention, a method of inhibiting proliferation of cancer cells is provided. This method involves contacting cancer cells with a powder from apple peel under conditions effective to inhibit proliferation of the cancer cells.

EXAMPLES

The following examples are provided to illustrate embodiments of the present invention but are by no means intended to limit its scope.

Example 1

Chemicals

Sodium nitrite, (+)-catechin, Folin-Ciocalteu reagent, citric acid, ascorbic acid, and α-keto-γ-methiolbutyric acid (KMBA) were purchased from Sigma Chemical Company (St. Louis, Mo.). Sodium carbonate, sodium hydroxide, ethanol, acetone, and potassium phosphate were obtained from Mallinckrodt (Paris, Ky.). Aluminum chloride, potassium chloride, and sodium acetate were purchased from Fisher Scientific (Pittsburgh, Pa.) and gallic acid from ICN Biomedical Inc. (Costa Mesa, Calif.). 2,2'-Azobis(amidinopropane) (ABAP) was obtained from Wako Chemicals (Richmond, Va.). The HepG$_2$ cells were from the American Type Culture Collection (ATCC) (Rockville, Md.) and the MTS-based Cell Titer 96 non-radioactive cell proliferation assay was from Promega (Madison, Wisc.). Williams Medium E (WME) and fetal bovine serum (FBS) were purchased from Gibco Life Technologies (Grand Island, N.Y.).

Example 2

Samples

Rome Beauty apples were obtained from Red Jacket Orchards (Geneva, N.Y.). The apples were kept in modified atmosphere storage until purchased. The apples were washed and dried before experimentation.

Example 3

Determination of Pretreatment Method

Five randomly selected apples were peeled using an Apple Master apple parer (Norpro®, Everett, Wash.). The peels were left untreated or were treated with citric acid dips, ascorbic acid dips, or boiling water dips (blanched). For the citric acid treatments, the five apple peels (approximately 75 g) were dipped for 3 minutes in 500 mL of 0.1, 0.2, 0.5, and 0.8% citric acid solutions, then drained. The ascorbic acid treatments involved dipping the peels in 0.1, 0.2, and 0.5% ascorbic acid for 3 minutes and draining. The blanching times were 1, 10, 20, and 30 seconds. After blanching, the peels were dipped in a cooling bath of distilled water for 10 seconds. The peels were placed in stainless steel wire baskets in a VWR 1325F Mechanical Convection oven (VWR Scientific Products, Bridgeport, N.J.) at 60° C. and remained there until they reached constant weight (approximately 13 hours). This temperature was chosen because earlier trials showed it to be quite damaging to phenolic compounds. Thus, any benefit from the treatments should have been easy to see. The dried apple peels were ground in a coffee grinder and stored at −40° C. until use. Each treatment (e.g., 0.1% citric acid) was performed in triplicate with different apple peels used each time.

Example 4

Determination of Drying Method

Five randomly selected apples were peeled using an Apple Master apple parer. The apple peels were treated with the best method from above. In addition, peels from another 5 apples were left untreated for comparison. The apple peels were oven-dried in a mechanical convection oven at 40, 60, or 80° C., air-dried in a fume hood, or freeze-dried. The oven-dried peels were placed in stainless steel wire baskets in a VWR 1325F Mechanical Convection Oven (VWR Scientific Products, Bridgeport, N.J.) at the appropriate temperature and remained there until the peels reached a constant weight. The air-dried peels were placed in stainless steel wire baskets in a fume hood and dried to constant weight. The freeze-dried peels were dried in a Virtis 100 SRC freeze-dryer (Virtis, Gardiner, N.Y.) in the pilot plant in the Department of Food Science, Cornell University (Ithaca, N.Y.). The condenser temperature was −40° C., the shelf temperature was set at 25° C., and the vacuum was 150 microns for 72 hours. The dried apple peels were ground in a coffee grinder and stored at −40° C. until use. Each drying trial was performed in triplicate.

Example 5

Extraction of Dried Apple Peels

The phytochemicals of dried apple peels were extracted by a method similar to that reported previously (Eberhardt et al., *Nature* 405:903-904 (2000); Dewanto et al., *J. Agric. Food Chem.* 50:3010-3014 (2002), each of which is hereby incorporated by reference in its entirety). Briefly, the dry equivalent of 25 g of apple peels was combined with 200 g chilled 80% acetone or chilled 80% ethanol solution and homogenized for 5 minutes using a Virtis 45 homogenizer (Virtis, Gardiner, N.Y.). The slurry was filtered through Whatman No. 1 filter paper in a Buchner funnel under vacuum. The filter cake was washed twice with 15 mL of the acetone or ethanol solution. The filtrate was recovered and evaporated using a rotary evaporator at 45° C. until less than 10% of the initial volume remained. The extract was made up to 50 mL with distilled water and frozen at −40° C. until analysis. All extracts were made in triplicate.

Example 6

Extraction of Fresh Apple Peels

The phytochemicals of apples were extracted by a method similar to that reported previously (Eberhardt et al., *Nature* 405:903-904 (2000); Dewanto et al., *J. Agric. Food Chem.* 50:3010-3014 (2002), each of which is hereby incorporated by reference in its entirety). Briefly, 25 g of apple peels were blended with 200 g chilled 80% acetone or chilled 80% ethanol solution in a Waring blender for 5 minutes. The sample was then homogenized for 3 minutes using a Virtis 45 homogenizer. The slurry was filtered through Whatman No. 1 filter paper in a Buchner funnel under vacuum. The solids were scraped into 150 g 80% acetone or ethanol and homogenized again for 3 minutes before refiltering. The filtrate was recovered and evaporated using a rotary evaporator at 45° C. until less than 10% of the initial volume remained. The extract was made up to 50 mL with distilled water and frozen at −40° C. until analysis. The extracts were made in triplicate.

Example 7

Determination of Total Phenolic Content

Total phenolic contents of the apple peel samples were measured using a modified colorimetric Folin-Ciocalteu method (Dewanto et al., *J. Agric. Food Chem.* 50:3010-3014 (2002); Singleton et al., *Methods Enzymol.* 299:152-178 (1999), each of which is hereby incorporated by reference in its entirety). Ethanol extracts were used in the analysis of apple peel treatments, while acetone extracts were used for evaluation of drying conditions and the scaled-up product. Volumes of 0.5 mL of deionized water and 0.125 mL of a known dilution of the extract were added to a test tube. Folin-Ciocalteu Reagent (0.125 mL) was added to the solution and allowed to react for six minutes. Then, 1.25 mL of 7% sodium carbonated solution was aliquoted into the test tubes and the mixture was diluted to 3 mL with deionized water. The color developed for 90 minutes and the absorbance was read at 760 nm using a MRX II DYNEX spectrophotometer (DYNEX Technologies Inc., Chantilly, Va.). The measurement was compared to a standard curve of gallic acid concentrations and expressed as mg gallic acid equivalents/100 g±SD fresh apple peels for the triplicate extracts.

Example 8

Deterinnation of Flavonoid Content

The flavonoid contents of the apple peel samples were measured using a modified colorimetric method (Dewanto et al., *J. Agric. Food Chem.* 50:3010-3014 (2002); Jia et al., *Food Chem.* 64:555-599 (1999), each of which is hereby incorporated by reference in its entirety). Ethanol extracts were used in the analysis of apple peel treatments, while acetone extracts were used for evaluation of drying conditions and the scaled-up product. A volume of 0.25 mL of a known dilution of extract was added to a test tube containing 1.25 mL distilled water. To the mixture, 0.075 mL of 5% sodium nitrite solution was added and allowed to stand for five minutes. Then, 0.15 mL of 10% aluminum chloride was added. After six minutes, 0.5 mL of 1M sodium carbonate was added and the mixture was diluted with another 0.275 mL distilled water. The absorbance of the mixture at 510 nm was measured immediately using a MRX II DYNEX spectrophotometer (DYNEX Technologies, Inc., Chantilly, Va.) and compared to a standard curve of catechin concentrations. The flavonoid content was expressed as mg catechin equivalents/100 g±SD fresh apple peels for the triplicate extracts.

Example 9

Determination of Anthocyanin Content

Monomeric anthocyanin contents of the apple peels was measured using a spectophotometric pH differential protocol (Boyles et al., *J. Food Sci.* 58:1135-1141 (1993); Liu et al., *J. Agric. Food Chem.* 50:2926-2930 (2002), each of which is hereby incorporated by reference in its entirety). The apple peel acetone extracts were mixed thoroughly with 0.025 M potassium chloride pH 1 buffer in 1:3 or 1:8 ratio of extract: buffer. The absorbance of the mixture was then measured at 515 and 700 nm against a distilled water blank. The apple peel extracts were then combined similarly with sodium acetate buffer (pH 4.5) and the absorbance of these solutions was measured at the same wavelengths. The anthocyanin content was calculated as follows:

Total monomeric anthocyanins (mg/100 g fresh peel)=A× MW×1000/($\epsilon$×C) where A is absorbance=$(A_{515}-A_{700})_{pH\,1.0}-(A_{515}-A_{700})_{pH\,4.5}$; MW is molecular weight for cyanidin 3-glucoside=449.2; $\epsilon$ is the molar absorptivity of cyanidin 3-glucoside=26,900; and C is the concentration of the buffer in mg/mL. Anthocyanin content was expressed as mg cyanidin 3-glucoside equivalents/100 g fresh apple peel for the triplicate extracts.

Example 10

Determination of Water Activity

Water activity is the ratio of the partial pressure of water vapor in a product to the saturation vapor pressure at equilibrium. It is a measure of the availability of water to participate in chemical reactions. Water activity was measured at approximately 28° C. using the AquaLab CX2 Water Activity Meter (Decagon Devices Inc., Pullman, Wash.). Each reading was done in triplicate.

Example 11

Quantification of Total Antioxidant Activity

The total antioxidant activity of the apple peels was determined using the total oxyradical scavenging (TOSC) assay (Winston et al., *Free Rad. Biol. Med.* 24:480-493 (1998), which is hereby incorporated by reference in its entirety) under modified conditions (Eberhardt et al., *Nature* 405:903-904 (2000), which is hereby incorporated by reference in its entirety). In this assay, peroxy radicals are formed from 2,2'-azobis-amidinopropane (ABAP) and oxidize $\alpha$-keto-$\gamma$-methiolbutyric acid (KMBA) to form ethylene. The ethylene produced can be measured by gas chromatographic headspace analysis. Total antioxidant activity is measured by the degree of inhibition of formation of ethylene by the apple peel acetone extracts.

The antioxidant activity was measured at 15, 30, 45, and 60 minutes for four different concentrations of the acetone extracts to determine the TOSC values. The area under the kinetic curve was integrated to calculate the TOSC value at each concentration as follows:

$$TOSC=100-(\int SA/\int CA)\times 100)$$

where $\int SA$ is the integrated area from the sample reaction and $\int CA$ is the integrated area from the control reaction. The median effective dose ($EC_{50}$) was determined for the apple peels from the dose-response curve of apple peel concentration versus TOSC. The antioxidant activity was expressed as micromoles vitamin C equivalents for 1 g of apple peel. The TOSC values were stated as mean±SD for triplicate samples.

Example 12

Determination of Inhibition of $HepG_2$ Cell Proliferation

The acetone extracts were used to measure the ability of apple peels to inhibit human liver cancer cell proliferation (Eberhardt et al., Nature 405:903-904 (2000); Liu et al., J. Agric. Food Chem. 50:2926-2930 (2002), each of which is hereby incorporated by reference in its entirety). The cell cultures were exposed to various concentrations of the apple peel extracts during a 96-hour growth period. The antiproliferative activity of the apple peel extracts was measured by the ability of viable cells to reduce 3-(4,5-dimethylthiazol-2-yl)-5-(3-carboxymethoxyphenyl)-2-(4-sulphenyl)-2H-tetrazolium (MTS) to formazan. This product absorbs light at 490 nm and was measured spectrophotometrically. The absorbance was measured using a MRX II DYNEX spectrophotometer (DYNEX Technologies, Inc., Chantilly, Va.). At least three replications for each sample were used to determine the inhibitory effect on cell proliferation. The effective median dose ($EC_{50}$) was calculated and expressed as mg apple peels/mL±SD.

Example 13

Statistical Analysis

All data was reported as mean±standard deviation of three replicates. The results were compared by analysis of variance (ANOVA) using Minitab software (Minitab, Inc., State College, Pa.). Pairwise multiple comparisons were done by Tukey's significant difference test with a family error rate of 0.05. Comparisons between blanched and unblanched samples were done by paired t-tests. Comparisons between the fresh apple peels and the scaled-up dried apple peels were done by 2-sample t-tests. Differences at $p<0.05$ were considered significant.

Example 14

Pretreatment Results

Rome Beauty apple peels were treated with citric acid dips, vitamin C dips, or blanched then oven-dried at 60° C. and evaluated for total phenolic content (FIG. 1). Fresh peels had more phenolics than the dried samples with 401.9±11.2 mg gallic acid equivalents/100 g fresh peels ($p<0.05$). The total phenolic content of the peels dipped in 0.1, 0.2, 0.5, and 0.8% citric acid solutions (137.2±14.2, 104.6±40.1, 102.1±0.9, and 107.3±20.9 mg gallic acid equivalents/100 g fresh peels, respectively) were not significantly different from each other ($p>0.05$). Remarkably, the untreated dried peels (Control, FIG. 1) had higher values than those treated with 0.2, 0.5, and 0.8% citric acid ($p<0.05$). The values for those samples dipped in 0.1, 0.2, and 0.5% vitamin C solutions were similar (152.9±37.1, 171.6±1.0, and 218.7±13.6 mg gallic acid equivalent/100 g fresh peel, respectively) ($p>0.05$). There was a trend for the phenolic content to increase with vitamin C concentration, though that trend was more likely due to the measurement of the added ascorbic acid, not endogenous phenolic compounds. The total phenolic content of the apple peels blanched for 1, 10, 20, and 30 seconds was 218.8±9.3, 258.1±45.2, 253.9±24.6, and 217.1±31.5 mg gallic acid equivalents/100 g fresh peels, respectively. There was no significant difference between these values ($p<0.05$). The apple peels blanched for 10 seconds and 20 seconds were statistically higher than those that were untreated or subjected to citric acid or vitamin C dips ($p<0.05$). The flavonoid content data mimicked the results of the total phenolic assay. As the peels blanched for 10 seconds had the highest total phenolic and flavonoid contents, that method was selected as the best method of treatment.

Example 15

Drying Results

Figure 2:
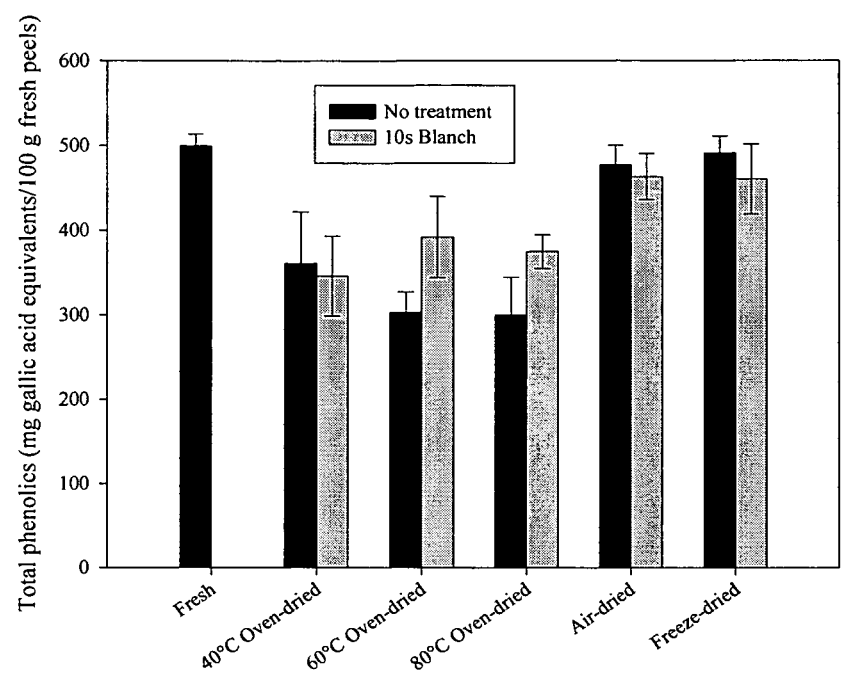
FIG. 2 is a graph showing total phenolic content of Rome Beauty apple peels dried under various conditions (mean±SD, n=3).

Rome Beauty apple peels were either blanched for 10 seconds or left untreated, then oven-dried at 40, 60, and 80° C., air-dried, or freeze-dried. The peels were extracted with 80% acetone and the total phenolic contents of the dried samples were analyzed (FIG. 2). The values for the fresh peels (500.2±13.7 mg gallic acid equivalents/100 g fresh peel), untreated air-dried peels (478.0±22.9 mg gallic acid equivalents/100 g fresh peel), and untreated freeze-dried peels (491.6±19.9 mg gallic acid equivalents/100 g fresh peel) were similar ($p>0.05$), and higher than the untreated oven-dried samples ($p<0.05$). The untreated peels dried at 40, 60, and 80° C. had similar total phenolic contents of 361.3±60.9, 303.4±24.2, and 300.4±44.4 mg/gallic acid equivalents/100 g fresh peels, respectively ($p>0.05$). The total phenolic contents of the air-dried blanched peels (463.7±27.3 mg/gallic acid equivalents/100 g fresh peels) and freeze-dried blanched peels (460.6±41.7mg/gallic acid equivalents/100 g fresh peels) were not different from that of the fresh peels ($p>0.05$). The 40, 60, and 80° C. oven-dried blanched peels had similar phenolic contents (346.0±47.2, 392.3±47.9, and 375.2±20.0 mg gallic acid equivalents/100 g fresh apple peels, respectively) ($p>0.05$) and the values were significantly lower than that of the fresh peels ($p<0.05$). There was no significant difference between total phenolic contents of the untreated and blanched peels under any drying condition.

Figure 3:
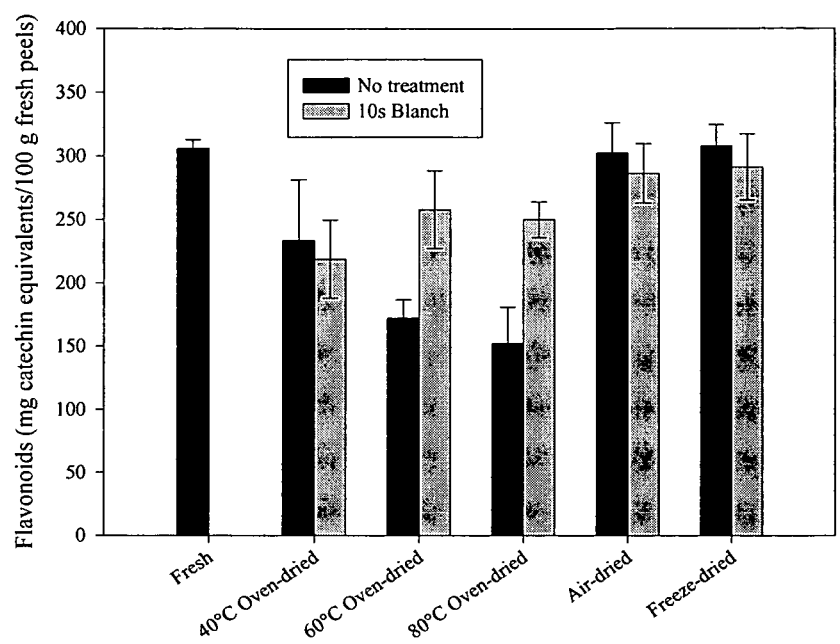
FIG. 3 is a graph showing total flavonoid content of Rome Beauty apple peels dried under various conditions (mean±SD, n=3).

The flavonoid contents of the untreated and blanched peels dried under various conditions were determined and compared to the flavonoid content of fresh apple peels (FIG. 3). The fresh peels had a flavonoid content of 306.1±6.7 mg catechin equivalents/100 g. The untreated air-dried and freeze-dried peels had similar contents with 302.8±23.5 and 308.0±16.7 mg catechin equivalents/100 g fresh peels ($p>0.05$). All untreated oven-dried peels had flavonoid contents that were significantly lower than the fresh peels and untreated freeze-dried peels ($p<0.05$). The values were 233.6±47.7, 172.3±14.4, and 152.2±28.7 mg catechin equivalents/100 g fresh peels for the untreated 40, 60, and 80° C. oven-dried peels, respectively. The fresh peels, blanched air-dried peels (286.4±23.4 mg catechin equivalents/100 g fresh peels), and blanched freeze-dried peels (291.4±26.1 mg catechin equivalents/100 g fresh peels) were higher in flavonoids than the blanched 40° C. oven-dried peels (218.8±30.8 mg catechin equivalents/100 g fresh peels) ($p<0.05$). The flavonoid contents of the blanched 60 and 80° C. oven-dried peels (257.9±30.7 and 250.1±14.1 mg catechin equivalents/100 g fresh peels, respectively) were similar to those of the fresh peels, blanched air-dried peels, and blanched freeze-dried peels ($p>0.05$). There were no significant differences between the flavonoid contents of the untreated and blanched peels under any drying condition ($p>0.05$).

Figure 4:
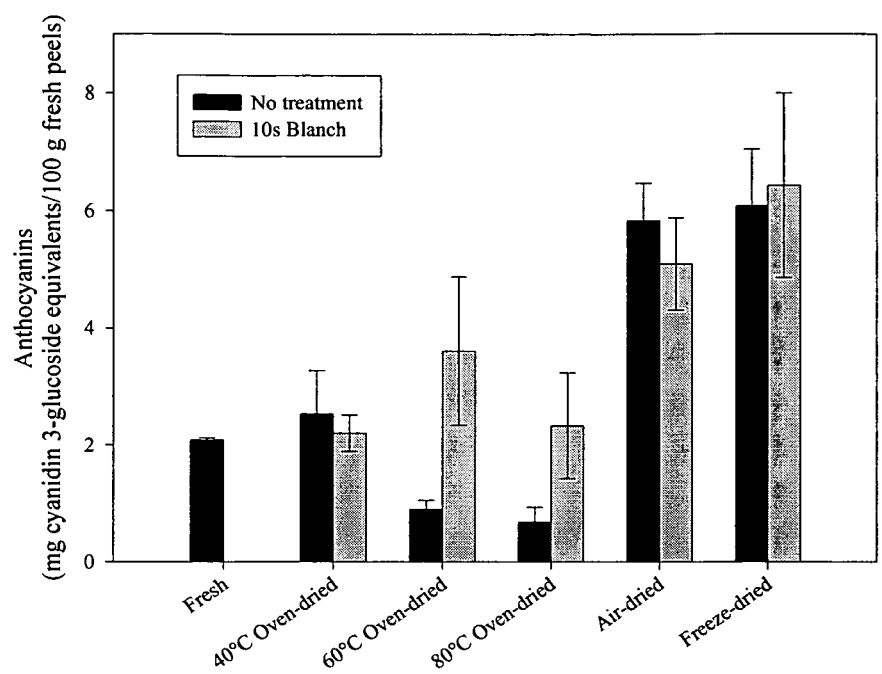
FIG. 4 is a graph showing anthocyanin content of Rome Beauty apple peels dried under various conditions (mean±SD, n=3).
Figure 5:
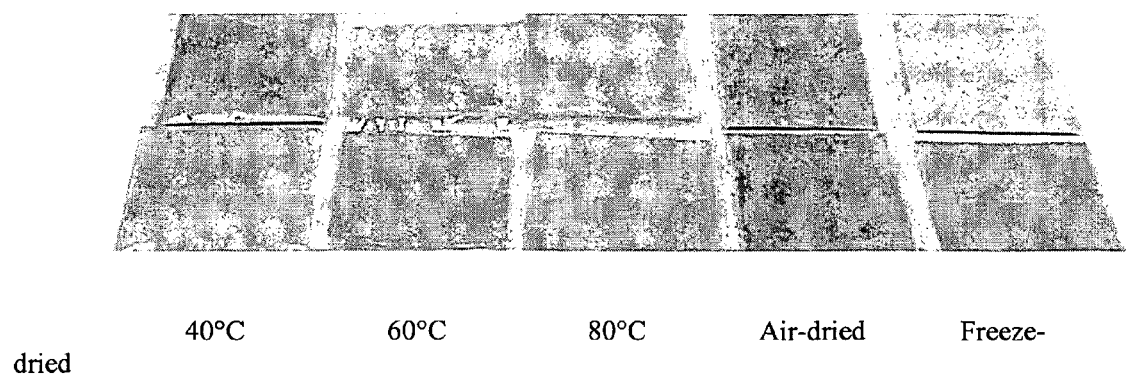
FIG. 5 is a photograph of the Rome Beauty apple peels dried under various conditions and ground to a powder. The top row samples are the untreated peels and the bottom row samples are the peels blanched for 10 seconds.

The anthocyanin contents of the apple peel extracts were measured (FIG. 4). The untreated air-dried and freeze-dried peels had similar anthocyanin contents (5.84±0.63 and 6.08±0.96 mg cyanidin 3-glucoside equivalents/100 g fresh peels, respectively) ($p>0.05$) and had higher contents than the fresh peels (2.09±0.03 mg cyanidin 3-glucoside equivalents/100 g) ($p<0.05$). The untreated oven-dried peels had similar anthocyanin contents to the fresh peels ($p>0.05$). The values were 2.09±0.03, 2.54±0.74, 0.90±0.16, 0.69±0.25 mg cyanidin 3-glucoside/100 g fresh peels for the untreated 40, 60, and 80° C. oven-dried peels, respectively. The blanched freeze-dried peels (6.43±1.57 mg cyanidin 3-glucoside/100 g fresh peels) contained more anthocyanins than the fresh peels ($p<0.05$) and had a similar content to the blanched air-dried peels (5.10±0.79 mg cyanidin 3-glucoside/100 g fresh peel). There was no difference between the anthocyanin contents of the blanched oven-dried peels (40, 60, and 80° C. peels had 2.20±0.31, 3.61±1.27, and 2.33±0.91 mg cyanidin 3-glucoside/100 g fresh peels, respectively) and the fresh peels ($p>0.05$). The anthocyanin contents of the untreated and blanched peels were similar at each temperature ($p>0.05$). The appearances of the apple peel powders showed that the blanched freeze-dried peels had the most desirable color (FIG. 5).

Figure 6:
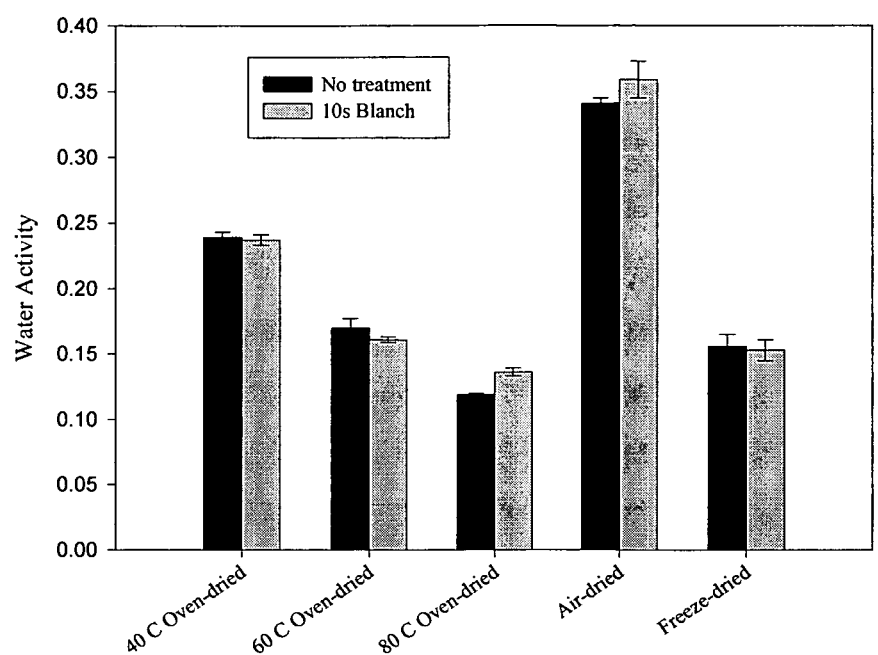
FIG. 6 is a graph showing water activity of Rome Beauty apple peels dried under various conditions (mean±SD, n=3).

The water activity of the apple peel powders was also measured (FIG. 6). Water activity ranged from 0.12 (blanched 80° C., oven-dried peels) to 0.36 (blanched, air-dried peels). There was no significant difference in water activities between the untreated and blanched peels under a given drying condition ($p>0.05$), except for the 80° C. oven-dried peels ($p<0.05$). The water activities of the peels decreased with increasing drying temperature for the oven-dried samples. The freeze-dried peels had water activities of 0.16±0.01 for the untreated peels, which was similar to the blanched peels (0.15±0.01) ($p>0.05$).

After reviewing the data, the peels were blanched for 10 seconds and freeze-dried to make the most stable food ingredient, with high phytochemical contents and desirable color. In order to better characterize the apple peel powder, the production was scaled up and the resulting ingredient was analyzed for phytochemical content, water activity, total antioxidant activity, and antiproliferative activity.

Example 16

Scale-Up

Figure 7:
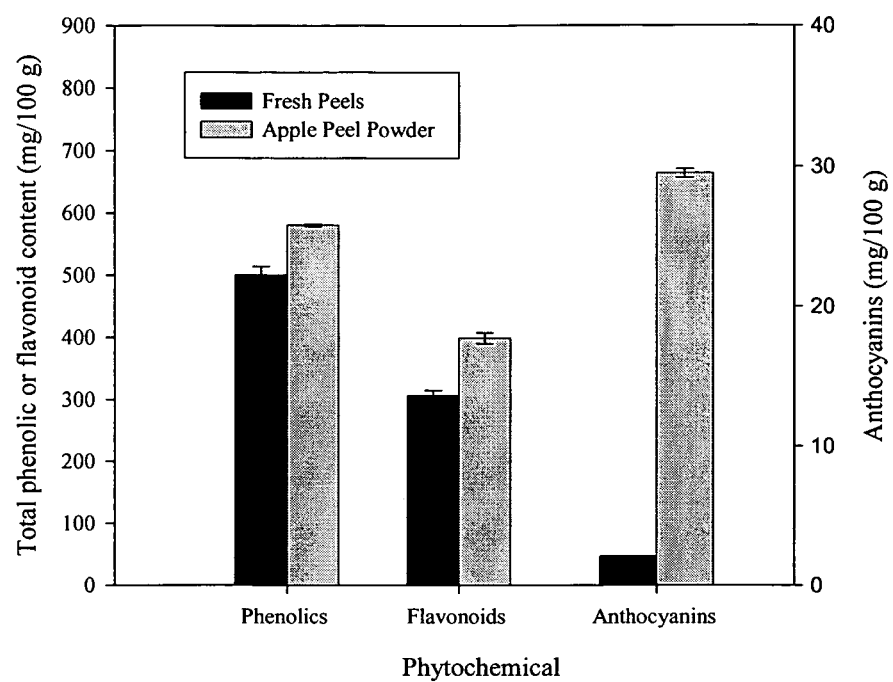
FIG. 7 is a graph showing phytochemical contents of the apple peel powder ingredient and fresh Rome Beauty apple peels. Total phenolics are expressed as mg gallic acid equivalents/100 g; flavonoids are expressed as mg catechin equivalents/100 g; and anthocyanins are expressed as mg cyanidin 3-glucoside/100 g. All are shown on a fresh weight basis (mean±SD, n=3).
Figure 8:
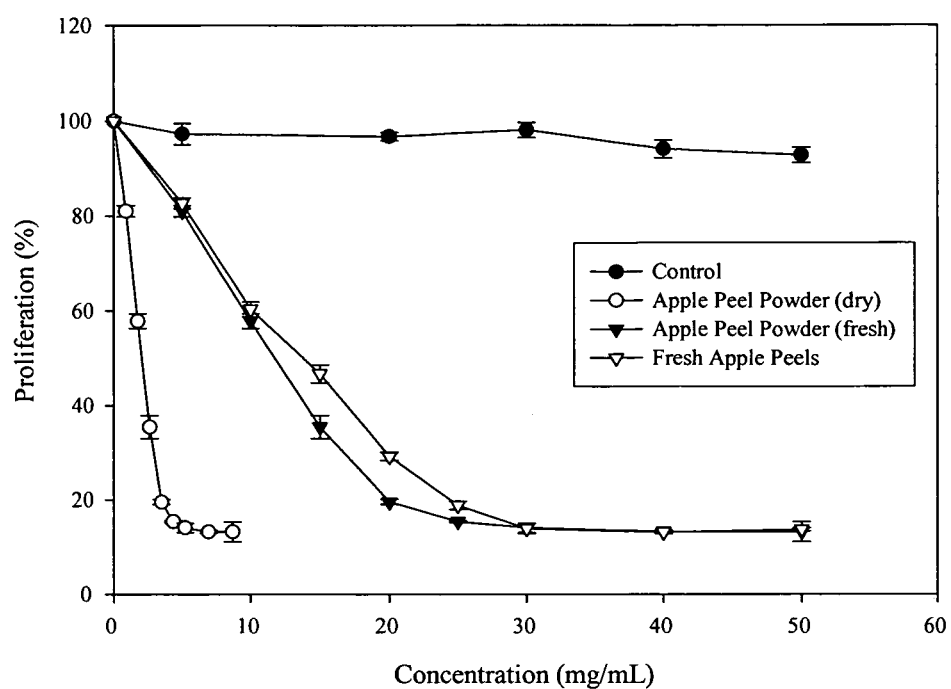
FIG. 8 is a graph showing inhibition of cell proliferation by apple peel powder ingredient and fresh Rome Beauty apple peels (mean±SD, n=3).

One hundred twenty Rome Beauty apples were peeled, blanched for 10 seconds, and freeze-dried as described above. The resulting dried peels were ground to a 60-mesh powder in a bench top hammermill and stored in sealed glass containers at −40° C. until analysis. The phytochemical contents of the apple peel powder ingredient and fresh apple peels are shown in FIG. 7. The freeze-dried apple peels had a total phenolic content of 3,342±12 mg gallic acid equivalents/100 g freeze-dried peels. For easier comparison with fresh peels, the phenolic content of the dried peels on a fresh weight basis was calculated to be 580.0±2.1 mg gallic acid equivalents/100 g fresh peels. This was significantly higher than the phenolic content of the fresh peels (401.9±11.2 mg gallic acid equivalents/100 g) on a fresh weight basis ($p<0.05$). The flavonoid content was 2,299±52 mg catechin equivalents/100 g freeze-dried peels, and was equivalent to 398.9±8.9 mg catechin equivalents/100 g fresh peels. Again, on a fresh basis, this was higher than the flavonoid content of fresh apple peels (306.1±6.7 mg catechin equivalents/100 g) ($p<0.05$). The anthocyanin content of the freeze-dried peels (170±2 mg cyanidin 3-glucoside equivalents/100 g or 29.5±0.3 mg cyanidin 3-glucoside equivalents/100 g fresh peels) was much higher than the anthocyanin content of the fresh peels (2.09±0.02 mg cyanidin 3-glucoside/100 g) ($p<0.05$). This is an apparent 14-fold increase in the anthocyanin content of the apple peels after blanching and freeze-drying. The apple peel powder had a total antioxidant activity of 1,251±56 µmol vitamin C equivalents/g (217.1±9.8 µmol vitamin C equivalents/g fresh peels). Thus, 1 g of dried apple peels had the same antioxidant value as 220 mg of vitamin C. On a fresh weight basis this was similar to the antioxidant activity of fresh Rome Beauty apple peels (223.6±6.5 µmol vitamin C equivalents/g) ($p>0.05$). The freeze-dried apple peels also had a strong antiproliferative activity on $HepG_2$ liver cancer cells (FIG. 8) with a median effective dose $EC_{50}$ of 1.88±0.01 mg/mL (10.83±0.03 mg fresh peels/mL). This was lower than the $EC_{50}$ of 12.41±0.36 mg/mL exhibited by the fresh apple peels ($p<0.05$). All values for the apple peel powder were significantly different from those of the fresh apple peels when compared on a dry weight basis ($p<0.05$).

In the above experiments, a value-added food ingredient was developed from Rome Beauty apple peels. This variety of apple is commonly used in applesauce manufacture in New York State. Thus, this could be a valuable use of the 20 million pounds of waste peels generated from applesauce and canned apple processing in New York state each year. The phytochemical content, antioxidant activity, and antiproliferative activity of the fresh peels were preserved through blanching the peels for 10 seconds followed by freeze-drying and grinding them to a powder. This apple peel powder ingredient could be added to various food products to enhance their nutritional values.

Polyphenoloxidase is responsible for enzymatic browning of apple tissue. When the cellular structure is broken during slicing and other processes, the compartmentalized enzyme is mixed with substrate. Chlorogenic acid is thought to be the main substrate for enzymatic browning reactions. Enzymatic browning can be controlled using heat inactivation of enzymes, sulfur dioxide or ascorbic acid treatments, deaeration, storage at low temperatures, or acidification with citric or malic acids (Shewfelt, *Flavor and Color of Fruits as Affected by Processing*, in *Commercial Fruit Processing*, Woodroof and Luh, Editors. 1986, AVI Publishing Company, Inc.: Westport. p. 481-529, which is hereby incorporated by reference in its entirety). The citric acid and ascorbic acid treatments were not effective in preventing oxidation of the phenolic compounds during oven-drying of the apple peels at 60° C. Heat inactivation by blanching the peels for 10 seconds was much more successful. Sulfur dioxide treatments were not used, as many people are hypersensitive to these compounds and producers of value-added products prefer to keep their labels "clean." Nonenzymatic browning of apples can also be a problem during dehydration. Heat increases this type of browning under low moisture conditions. It is best to obtain the lowest moisture content possible with minimal heat damage to prolong the shelf-life of dried apples (Shewfelt, *Flavor and Color of Fruits as Affected by Processing*, in *Commercial Fruit Processing*, Woodroof and Luh, Editors. 1986, AVI Publishing Company, Inc.: Westport. p. 481-529, which is hereby incorporated by reference in its entirety). Consistent with this, the air-dried and freeze-dried apple peels retained their phenolic compounds better than the oven-dried samples.

A slight, insignificant decrease in the phenolic and flavonoid contents of air-dried and freeze-dried apple peels that were blanched for 10 seconds was observed when compared to the untreated peels. This was likely due to leaching of the compounds into the boiling water. This loss of phytochemicals during blanching has been noted in other produce. Broccoli that was steam-blanched or water-blanched for four minutes showed large losses of glucosinolates, with the water blanch leading to greater losses due to leaching (Goodrich, *J. Food Proc. Preserv.* 13:275-280 (1989), which is hereby incorporated by reference in its entirety). The 10 second duration of the apple peel blanch was probably not long enough to lead to great phytochemical losses. Despite the slightly lower flavonoid and phenolic contents, the appearances of the apple peel powders made from blanched peels was much more red and appealing than the powders made from unblanched apple peels. The color compounds, anthocyanins, can be degraded by glycosidases, polyphenoloxidases, and peroxidases (Delgado-Vargas et al., *Crit. Rev. Food Sci. Nutr.*, 40:173-289 (2000), which is hereby incorporated by reference in its entirety). Thus, blanching likely inactivated these deleterious enzymes and preserved the color of the apple peels.

Based on the collected data, it is believed that the blanched freeze-dried peels would be the best choice for a food ingredient. Although the freeze-dried peels did not have significantly different phenolic, flavonoid, or anthocyanin contents from the air-dried peels, they did have a lower water activity. The decreased water activity could allow for greater chemical stability and increased shelf-life of the apple peel powder. Apple pomace extracts dried on maltodextrin that had water activities lower than 0.3 had a much longer shelf-life than those with higher water activities (Delgado-Vargas et al., *Crit. Rev. Food Sci. Nutr.*, 40:173-289 (2000), which is hereby incorporated by reference in its entirety). The untreated freeze-dried peels had similar phytochemical contents and water activity to the blanched peels. However, the presence of potentially active enzymes in the untreated peels could lead to problems with the apple peel powder during storage and in food applications. Peels blanched for 10 seconds and freeze-dried before being ground to a powder would make the most stable product.

Unexpectedly, on a fresh weight basis the freeze-dried peels contained significantly higher phytochemical contents than the fresh peels and exhibited higher antiproliferative activity. The Rome Beauty apples used in the scale-up were purchased a few months later than the ones used in the fresh peels analysis. However, they were grown at the same orchard and in the same season. It has been shown that seasonal variations of specific phytochemicals in a particular apple cultivar appear to be small in most cases (van der Sluis et al., *J. Agri. Food Chem.* 49:3606-3613 (2001), which is hereby incorporated by reference in its entirety), and cold storage of apples does not substantially affect the flavonoid and chlorogenic acid content of apple peels (Golding et al., *J. Agri. Food Chem.* 49:2283-2289 (2001); Awad et al., *Postharvest Biol. Technol.* 20:15-24 (2000), each of which is hereby incorporated by reference in its entirety). Other factors have much larger influences on the phytochemical content of apples. The apple variety (van der Sluis et al., *J. Agri. Food Chem.* 49:3606-3613 (2001), which is hereby incorporated by reference in its entirety) and the amount of light the apples receive (Awad et al., *Sci. Hortic.* 88:289-298 (2001), which is hereby incorporated by reference in its entirety), affect some phenolic concentrations. It was determined that concentrations of catechins, phloridzin, and chlorogenic acid in the peel of Jonagold apples are independent of light exposure; however, shading decreases levels of cyanidin 3-galactoside and quercetin 3-glycosides (Awad et al., *Sci. Hortic.* 88:289-298 (2001), which is hereby incorporated by reference in its entirety). The particular orchard that the apples are grown in can influence flavonoid content, possibly due to differences in shading and soil nutrient availability (Awad et al., *Sci. Hortic.* 83:249-263 (2000), which is hereby incorporated by reference in its entirety). Thus, the differences between the apple peel powder and the fresh apple peels could be accounted for by the variations in the amount of light the apples received. Another explanation is that the processing conditions could release bound phenolic compounds and make them available for measurement, as over 50% of phenolics in apples are conjugated (Vinson et al., *J. Agric. Food Chem.* 49:5315-5321 (2001), which is hereby incorporated by reference in its entirety). Lycopene in tomatoes (Dewanto et al., *J. Agric. Food Chem.* 50:3010-3014 (2002), which is hereby incorporated by reference in its entirety) and ferulic acid in corn (Dewanto et al., *J. Agric. Food Chem.* 50:4959-4964 (2002), which is hereby incorporated by reference in its entirety) is released in this manner during heat processing.

The apple peel powder ingredient of the present invention could be a valuable and attractive addition to healthy food products. A small amount could greatly increase the phytochemical content and antioxidant activity of foods. Applications may include cereals, granola bars, fruit leathers, sports bars, and fruit smoothies. Inclusion of phytochemical-rich apple peels in a diet rich in fruits, vegetables, and whole grains could assist in the prevention and management of chronic diseases.

Example 17

Samples

Cortland and Idared apples were purchased from Cornell Orchards (Cornell University, Ithaca, N.Y.). Rome Beauty and Golden Delicious apples were obtained from Red Jacket Orchards (Geneva, N.Y.). All apples were kept in modified atmosphere storage until purchased. The apples were washed and dried before analysis. They were peeled, when necessary, with an Apple Master apple parer and cored. The flesh, flesh+peel, or peels were obtained from 5 randomly selected apples in each trial to minimize variation. The flesh was the edible portion of the apple without the peel. The flesh+peel was the edible portion of the apple with the amount of flesh and peel maintained in the same proportions as in the whole apple. The peels were the parts of the apple removed by the apple parer.

Example 18

Extraction

The phenolic compounds of apples were extracted by a method similar to that reported previously (Eberhardt et al., *Nature* 405:903-904 (2000); Dewanto et al., *J. Agric. Food*

Chem. 50:3010-3014 (2002), each of which is hereby incorporated by reference in its entirety). Briefly, 50 g of apple flesh or apple flesh with the peel was blended with 200 g chilled 80% acetone solution in a Waring blender for 5 minutes. The sample was then homogenized for 3 minutes using a Virtis 45 homogenizer. The slurry was filtered through Whatman No. 1 filter paper in a Buchner funnel under vacuum. The solids were scraped into 150 g 80% acetone and homogenized again for 3 minutes before refiltering. The filtrate was recovered and evaporated using a rotary evaporator at 45° C. until less than 10% of the initial volume remained. The extract was made up to 50 mL with distilled water and frozen at −40° C. until analysis. Apple peels were extracted similarly using 25 g peel. All extracts were made in triplicate.

Example 19

Content of Phenolic Compounds

Figure 9:
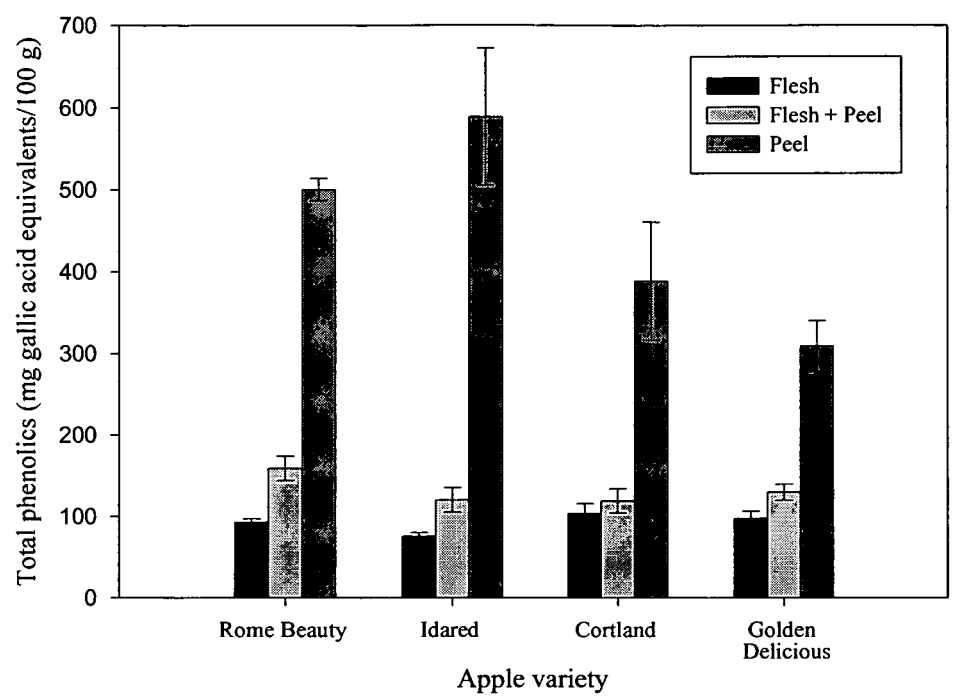
FIG. 9 is a graph showing total phenolic content of apples (mean±SD, n=3).

Total phenolic contents of the flesh, flesh+peel, and peel of the four apple varieties were determined (FIG. 9). Of the peels, the total phenolic content of Idared and Rome Beauty peels were highest ($p<0.05$) at 588.9±83.2 and 500.2±13.7 mg gallic acid equivalents/100 g peels, respectively, followed by 388.5±82.4 for Cortland, and 309.1±32.1 for Golden Delicious apples. The flesh+peel values were 159.0±15.1, 129.7±9.7, 120.1±15.0, and 119.0±14.9 mg gallic acid equivalents/100 g flesh+peel for Rome Beauty, Golden Delicious, Idared, and Cortland apples, respectively. These values were not significantly different ($p>0.05$). The total phenolic contents of the flesh of Cortland (103.2±12.3 mg gallic acid equivalents/100 g flesh), Golden Delicious (97.7±8.9), and Rome Beauty (93.0±4.1) apples were similar ($p>0.05$). The flesh of Idared apples had a lower phenolic content (75.7±4.0 mg gallic acid equivalents/100 g flesh) than the flesh of Cortland and Golden Delicious apples ($p<0.05$). The total phenolic content tended to be highest in the peel, followed by the flesh+peel and the flesh for all four apple varieties. The total phenolic contents of the peels were significantly higher than the flesh and flesh+peel values within all varieties ($p<0.05$), while phenolic contents of the flesh samples were not significantly lower than the flesh+peels contents ($p>0.05$). The flesh and flesh+peel values were similar for Idared, Cortland, and Golden Delicious apples ($p>0.05$).

Figure 10:
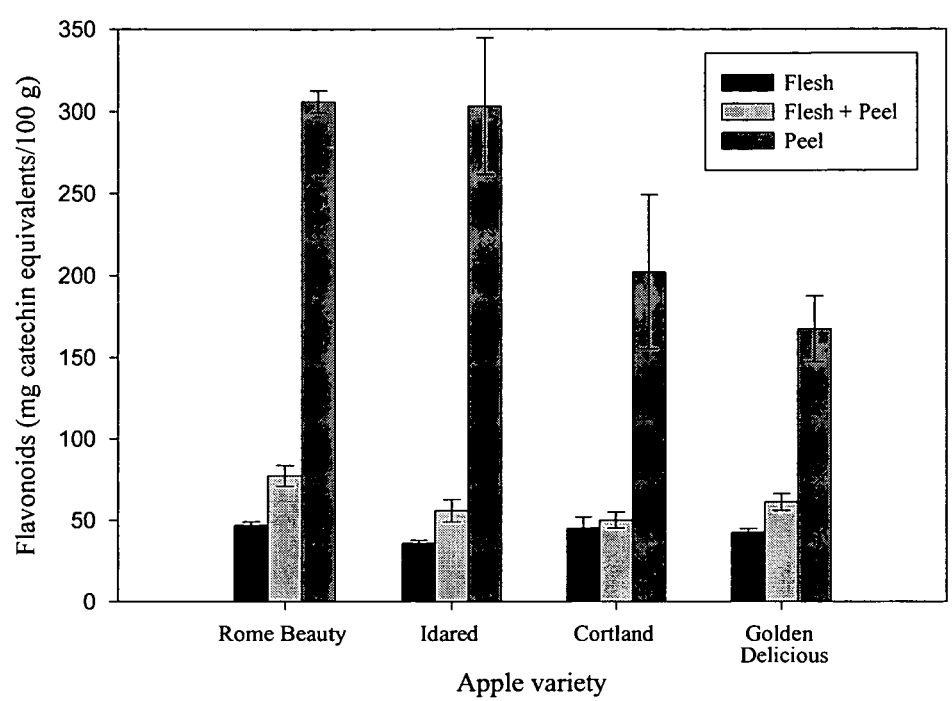
FIG. 10 is a graph showing flavonoid content of apples (mean±SD, n=3).

The soluble flavonoids of the apple components were measured (FIG. 10). The peels of Rome Beauty and Idared apples had the highest flavonoid contents (306.1±6.7 and 303.2±41.5 mg catechin equivalents/100 g peel, respectively). The flavonoid contents of Rome Beauty and Idared apple peels were not significantly different ($p>0.05$), and were higher than the contents of the peels from Cortland and Golden Delicious apples ($p<0.05$). The values for the peels of the Cortland and Golden Delicious apples were similar at 202.2±47.1 for Cortland, and 167.4±20.2 mg catechin equivalents/100 g peel for Golden Delicious apples ($p>0.05$). The flavonoid contents of the flesh+peel components of the apples were, in descending order, 77.1±6.4, 61.0±5.1, 55.8±6.8, and 50.0±4.9 mg catechin equivalents/100 g flesh+peel for Rome Beauty, Golden Delicious, Idared, and Cortland, respectively. The Rome Beauty flesh+peel possessed significantly more flavonoids than the flesh+peel of the other varieties ($p<0.05$), which all had similar flavonoid contents ($p>0.05$). The flesh contained 46.8±2.3 (Rome Beauty), 45.0±7.0 (Cortland), 42.5±2.3 (Golden Delicious), and 35.7±2.0 (Idared) mg catechin equivalents/100 g flesh. Only the flavonoid contents of the flesh of Rome Beauty and Idared apples were significantly different ($p<0.05$). Within all varieties, the peels tended to contain the most flavonoids, followed by the flesh+peel and the flesh. The flavonoid contents of the peels were statistically higher than the flesh and flesh+peel values for each variety ($p<0.05$). Only for Rome Beauty apples was the flavonoid content of the flesh+peel significantly higher than that of the flesh ($p<0.05$).

Figure 11:
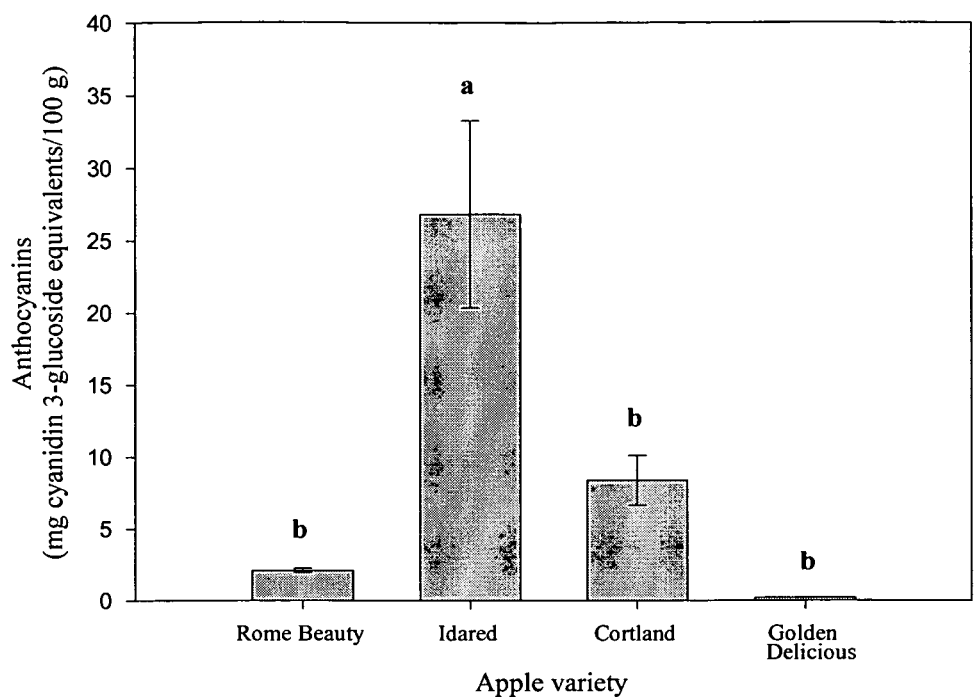
FIG. 11 is a graph showing anthocyanin content of apple peels (mean ±SD, n=3). Bar values with no letters in common are significantly different (p<0.05).

The anthocyanins in the apple peels were quantified (FIG. 11). The anthocyanin content of the flesh and flesh+peel were not analyzed as apple flesh of these varieties does not contain anthocyanins. The anthocyanin content of Idared apple peels was the highest at 26.8±6.5 mg cyanidin 3-glucoside equivalents/100 g peels ($p<0.05$), followed by Cortland (8.4±1.7) and Rome Beauty (2.1±0.2). Golden Delicious apple peels contained a trace amount of anthocyanins. The anthocyanin content of Idared peels was significantly higher than the content of the peels of the other varieties ($p<0.05$). There were no significant differences in the anthocyanin contents of Cortland, Rome Beauty, and Golden Delicious peels ($p>0.05$).

Example 20

Total Antioxidant Activity

Figure 12:
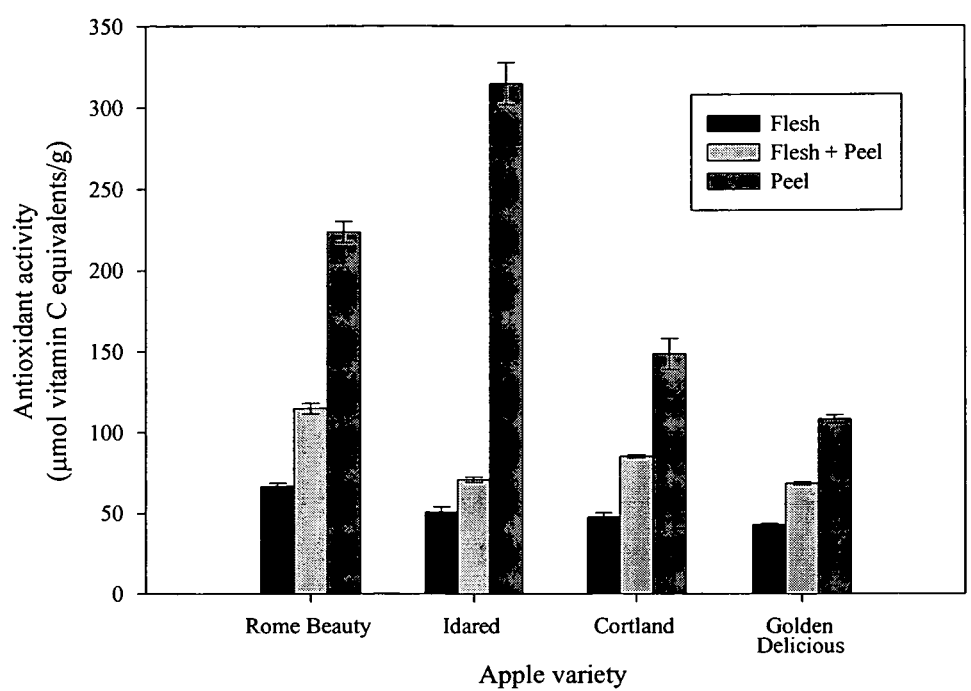
FIG. 12 is a graph showing the antioxidant activity of apples (mean±SD, n=3).

The total antioxidant activity of the peels was greater than that of the flesh or flesh+peel for all varieties (FIG. 12). Idared peel possessed the greatest activity, with 312.2±9.8 μmol vitamin C equivalents/g peel. The peels of Rome Beauty, Cortland, and Golden Delicious apples had total antioxidant activities of 228.4±6.7, 159.0±4.3, and 111.4±4.7 μmol vitamin C equivalents/g peel, respectively. All peel values of antioxidant activity were significantly different ($p<0.05$). The flesh+peel of Rome Beauty apples had the highest antioxidant activity (131.6±0.8 μmol vitamin C equivalents/g flesh+peel) when compared to that component of the other apples (72.2±2.3, 83.5±2.3, and 66.9±1.8 μmol vitamin C equivalents/g flesh+peel for Idared, Cortland, and Golden Delicious, respectively). The antioxidant activities of the flesh+peel components were statistically different ($P<0.05$) between varieties except there was no difference between the values for Idared and Golden Delicious flesh+peel ($p>0.05$). In descending order, the flesh components had total antioxidant activities of 68.02±1.47 (Rome Beauty), 50.4±2.2 (Cortland), 46.9±1.6 (Idared), and 43.5±0.4 (Golden Delicious) μmol vitamin C equivalents/g flesh. The flesh antioxidant activity of Rome Beauty apples was significantly higher than that of the other varieties ($p<0.05$). There were no differences among the antioxidant activities of the flesh of Cortland, Idared, and Golden Delicious apples ($p>0.05$). The antioxidant activity was highest from the peels in all varieties, followed by the flesh+peel and the flesh ($p<0.05$).

Example 21

Inhibition of Cancer Cell Proliferation

Figure 13:
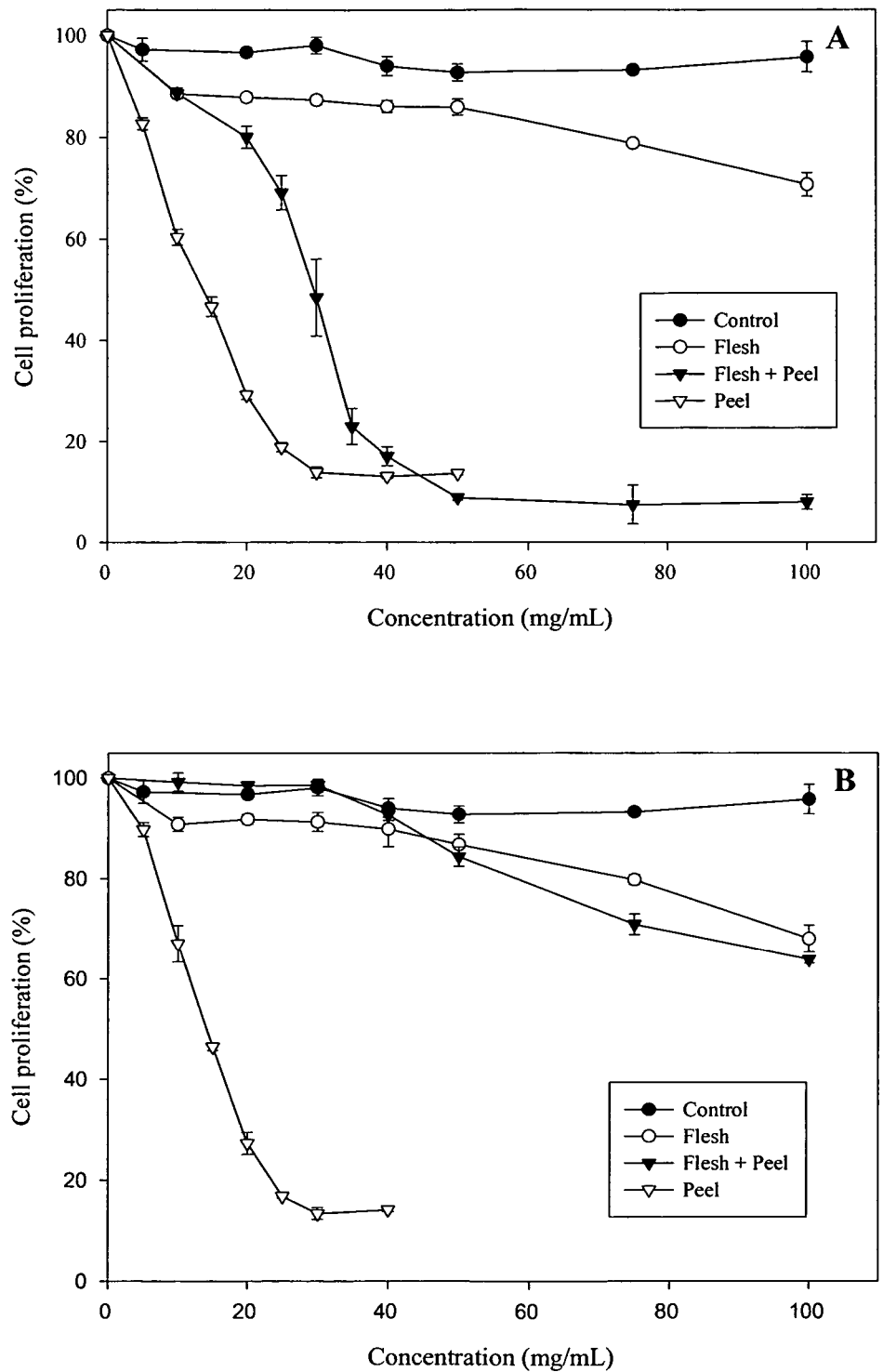
FIGS. 13A, B, C, and D are graphs showing inhibition of HepG$_2$ human liver cancer cell proliferation by phytochemical extracts of Rome Beauty (FIG. 13A), Idared (FIG. 13B), Cortland (FIG. 13C), and Golden Delicious (FIG. 13D) apples (mean±SD, n=3).
Figure 13:
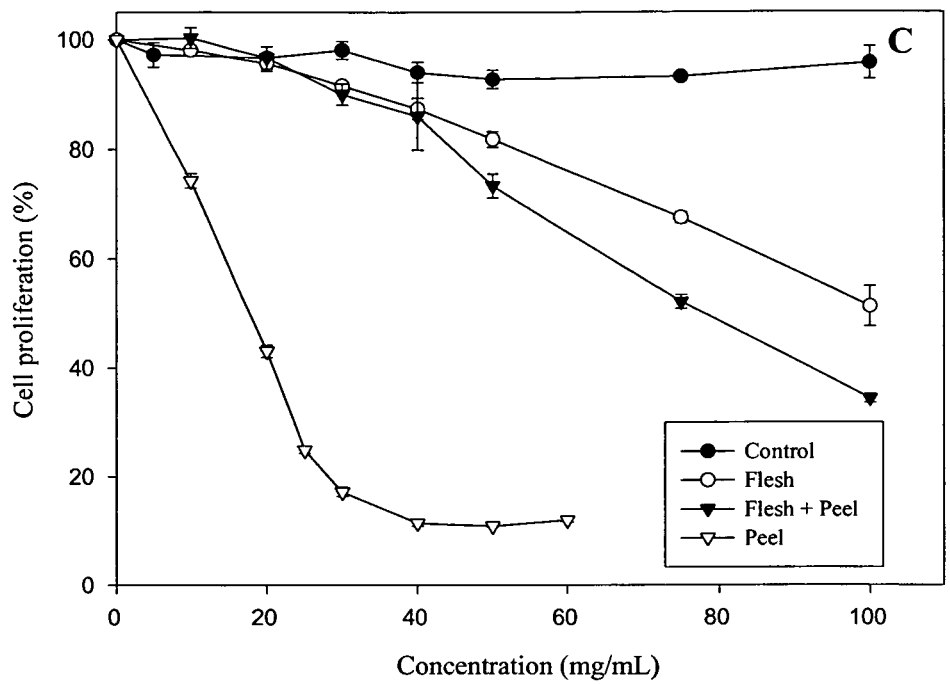
Figure 13:
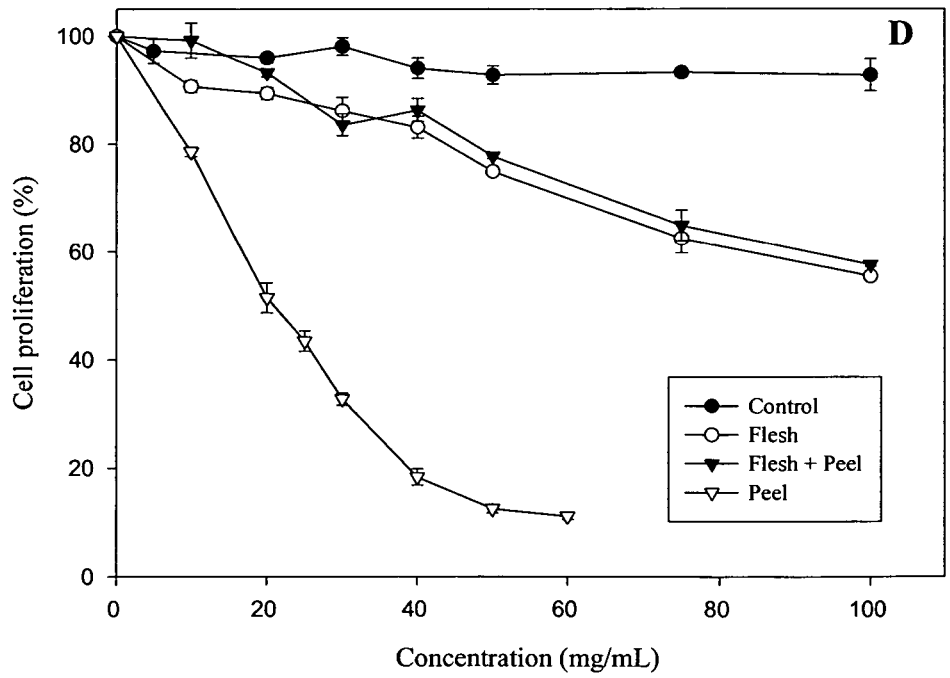

The effect of apple flesh, flesh+peel and peels on the growth of HepG$_2$ cells in vitro was summarized in FIGS. 13A-D. The curves showed that liver cancer cell growth was inhibited in a dose-dependent manner. The flesh and flesh+peel curves had similar slopes for most of the varieties; however, the flesh+peel of Rome Beauty apples was unusually inhibitory (FIG. 13A). Table 1 shows the EC$_{50}$ of the antiproliferative activity of different apple varieties. Lower EC$_{50}$ values represent higher antiproliferative activities.

TABLE 1

EC$_{50}$ for the inhibition of HepG$_2$ human liver cancer cell proliferation by phytochemical extracts of apples (mean ± SD, n = 3).

| Apple Variety | Flesh (mg/mL) | Flesh + Peel (mg/mL) | Peel (mg/mL) |
|---|---|---|---|
| Rome Beauty | * | 26.5 ± 0.3 | 12.4 ± 0.4 |
| Idared | * | 125.1 ± 58.8 | 13.6 ± 0.2 |
| Cortland | 103.9 ± 16.5 | 74.1 ± 4.0 | 15.7 ± 0.3 |
| Golden Delicious | 155.3 ± 11.7 | 107.7 ± 22.7 | 20.2 ± 0.7 |

* The EC$_{50}$ value could not be calculated from the dose-response curve

Rome Beauty apples had the lowest EC$_{50}$ values for the peel and flesh+peel components at 12.4±0.4 and 26.5±0.3 mg apple/mL, respectively, indicating the most antiproliferative activity of the varieties examined (p<0.05). The differences in the activities of the peels between varieties were significant (p<0.05). All the values were similar for the flesh+peel (p>0.05), except Rome Beauty apples were statistically more inhibitive than Idared (p<0.05). Cortland and Golden Delicious flesh had similar EC$_{50}$ values (p>0.05). The inhibition of cell proliferation by Rome Beauty flesh and Idared flesh were not adequate to calculate their EC$_{50}$ values. The peels of each apple variety inhibited the growth of HepG$_2$ cells more than the flesh or flesh+peel, and the peels had low EC$_{50}$ values compared to the flesh and flesh+peel components. The EC$_{50}$ doses were significantly different between the peel, flesh+peel and flesh of Rome Beauty, Cortland, and Golden Delicious apples (p<0.05). There was no statistical difference between the EC$_{50}$ values of the peel and flesh+peel of Idared apples (p>0.05). This may be due to the high variation of data collected from Idared apples.

Correlations between total phenolics, total antioxidant activity, and cell proliferation EC$_{50}$ values were analyzed for the flesh, flesh+peel, and peels of the apples. Total antioxidant activity was highly correlated to cancer cell inhibition for the flesh+peel extracts (R$^2$=0.939, p<0.05). There were no other significant relationships observed.

Apple peels are a waste product from applesauce and canned apple manufacture. In the year 2000 in New York State, 216 million pounds of apples were processed in this manner (USDA, *National Agriculture Statistics Service.* (2001), which is hereby incorporated by reference in its entirety), resulting in an estimated production of almost 16 million pounds of waste apple peels. Thus, a valuable source of nutrition may be removed from the food chain.

It is shown herein that apple peels possess high contents of phenolic compounds compared to other edible parts of the apple. The total phenolic and flavonoid contents for the flesh and flesh+peel samples were comparable to those previously reported (Podsedek et al., *Eur. Food Res. Technol.* 210:268-272 (2000); Liu et al., *N.Y. Fruit Q.* 9:15-17 (2001), each of which is hereby incorporated by reference in its entirety). Other research groups have also noted that apple peels had higher phenolic content than the flesh (Burda et al., *J. Agric. Food Chem.* 38:945-948 (1990); Ju et al., *Postharvest Biol. Technol.* 8:83-93 (1996); Escarpa et al., *J. Chromatogr.* 823:331-337 (1998), each of which are hereby incorporated by reference in its entirety). The nature and distribution of these phenolics between the flesh and the peel of the apple is also different. Among others, the flesh contains catechins, procyanidins, phloridzin, phloretin glycosides, caffeic acid and chlorogenic acid; the peel possesses all of these compounds and has additional flavonoids not found in the flesh, such as quercetin glycosides (Burda et al., *J. Agric. Food Chem.* 38:945-948 (1990); Escarpa et al., *J. Chromatogr.* 823:331-337 (1998); Golding et al., *J. Agric. Food Chem.* 49:2283-2289 (2001); van der Sluis et al., *J. Agric. Food Chem.* 49:3606-3613 (2001), each of which is hereby incorporated by reference in its entirety). Of the catechins, only (+)-catechin and (−)-epicatechin are present in appreciable amounts in apples (Arts et al., *J. Agric. Food Chem.* 48:1746-1751 (2000), which is hereby incorporated by reference in its entirety), with epicatechin being approximately twice as concentrated as catechin in the peels (Golding et al., *J. Agric. Food Chem.* 49:2283-2289 (2001), which is hereby incorporated by reference in its entirety). The most common procyanidins, oligomers of epicatechin, are procyanidin B2, procyanidin B5, and procyanidin trimer (Golding et al., *J. Agric. Food Chem.* 49:2283-2289 (2001); Lister et al., *J. Sci. Food Agric.* 64:155-161 (1994), each of which is hereby incorporated by reference in its entirety). Lister et al. (1994), reported quercetin glycoside concentrations of 400-700 mg/100 g and 250-550 mg/100 g in Granny Smith and Splendour apple peels, respectively, with quercetin 3-galactoside (hyperin), quercetin 3-arabinofuranoside (avicularin), quercetin 3-rhamnoside (quercitin), and quercetin 3-xyloside (reynoutrin) being the four most common. Golding et al. (2001), found similar levels of the flavonols in peels, recording values of 99-300 mg/100 g. Phloridzin and chlorogenic acid levels were quite low in the peel compared to in the flesh (Awad et al., *Sci. Hortic.* 83:249-263 (2000), which is hereby incorporated by reference in its entirety).

The measured anthocyanin content of the apple peels was related to their appearances. The red color of apple peels is due to the presence of cyanidin 3-galactoside (Awad et al., *Postharvest Biol. Technol.* 20:15-24 (2000), which is hereby incorporated by reference in its entirety). The Idared apples were deep red in color and had the most anthocyanins. The Cortland apples were bright red with green patches and the Rome Beauty apples were pink. Both varieties had far less anthocyanins than the Idareds. Golden Delicious apple peels were almost devoid of anthocyanins, as expected by their lack of red pigmentation.

It is believed that this is the first time the total antioxidant activity of apple peels has been measured. The peels of the apple varieties investigated herein exhibited high antioxidant activity when compared to the flesh and flesh+peel (p<0.05). The peels from one average-sized Idared apple had an antioxidant activity equivalent to 820 mg vitamin C. The antioxidant activity of the edible portion of apples has been ascertained in the past using the oxygen radical absorbance capacity assay (ORAC). Wang et al., *J. Agric. Food Chem.* 44:701-705 (1996), which is hereby incorporated by reference in its entirety, ranked apples ninth out of twelve fruits, and Vinson et al., *J. Agric. Food Chem.* 49:5315-5321 (2001), which is hereby incorporated by reference in its entirety, placed them eighth out of twenty. Using the TOSC assay, apples exhibited high total antioxidant activity and the value varied between apple varieties (Eberhardt et al., *Nature* 405:903-904 (2000), which is hereby incorporated by reference in its entirety). There was also a positive relationship between the phenolic content of apples and their antioxidant activity (Liu et al., *N.Y. Fruit Q.* 9:15-17 (2001), which is hereby incorporated by reference in its entirety). Apple extracts are able to bind to plasma low density and very low density lipoproteins and inhibit their oxidation (Vinson et al., *J. Agric. Food Chem.* 49:5315-5321 (2001), which is hereby incorporated by reference in its entirety).

The peels of Rome Beauty, Idared, Cortland and Golden Delicious apples greatly inhibited the growth of liver tumor cells in vitro. The flesh+peel and flesh samples also showed inhibitory effects in most cases, though they showed much less antiproliferative activity than the peels. Liu et al., *N.Y. Fruit Q.* 9:15-17 (2001), which is hereby incorporated by reference in its entirety, likewise reported antiproliferative effect from phytochemical extracts of Fuji, Gala, and Red Delicious apples on human liver cancer cells. Interestingly, Rome Beauty flesh+peel had a low $EC_{50}$ value compared to the flesh+peel of the other varieties, despite the lack of growth inhibition by the flesh alone. This may indicate some synergistic effects between the phytochemicals of the flesh and peel of this variety.

The antiproliferative ability of apple peels had not been investigated previously. The peels of Rome Beauty, Idared, Cortland and Golden Delicious apples greatly inhibited the growth of liver tumor cells in vitro. The flesh+peel and flesh samples also showed inhibitory effects in most cases, though they showed much less antiproliferative activity than the peels. Liu et al. (*N.Y. Fruit Q.* 9:15-17 (2001), which is hereby incorporated by reference in its entirety), likewise reported antiproliferative effect from phytochemical extracts of Fuji, Gala, and Red Delicious apples on human liver cancer cells. Interestingly, Rome Beauty flesh+peel had a low $EC_{50}$ value compared to the flesh+peel of the other varieties, despite the lack of growth inhibition by the flesh alone. This may indicate some synergistic effects between the phytochemicals of the flesh and peel of this variety.

These results show that eating apple peels may have health benefits for consumers. Apple peels are often discarded in the production of processed apple products, but clearly possess high levels of antioxidant and bioactive compounds. Waste apple peels from applesauce and canned apple manufacture should be regarded as a valuable product. It is believed they show potential as a functional food or value-added ingredient in the future. As part of a diet rich in fruits, vegetables and grains, apples and their peels may assist in the prevention of chronic disease.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A powder obtained from apple peel that has been subjected to phytochemical preservation wherein the powder has a phenolic content and a flavonoid content similar to fresh apple peel on a fresh weight basis, wherein the powder has a water activity of less than 0.30 and the phenolic content of the powder is at least about 92% of the phenolic content of fresh apple peel.

2. The powder according to claim 1, wherein the powder comprises flavonoids in a concentration of about 250-450 mg catechin equivalents per 100 grams of fresh apple peel.

3. The powder according to claim 1, wherein the powder comprises anthocyanins in a concentration of about 1-50 mg cyanidin 3-glucoside equivalents per 100 grams of fresh apple peel.

4. The powder according to claim 1, wherein the powder has an antioxidant activity of about 200-300μmol vitamin C equivalents per 1 gram of fresh apple peel.

5. The powder according to claim 1, wherein the powder has antiproliferative activity with a median effective dose $EC_{50}$ of about 9-15 mg fresh apple peel/mL.

6. A capsule comprising the powder according to claim 1.

7. A tablet comprising the powder according to claim 1 in compressed form.

8. A foodstuff comprising the powder according to claim 1.

9. The foodstuff according to claim 8, wherein the foodstuff is selected from the group consisting of sauce, tea, candy, cereals, breads, fruit mixes, fruit salads, salads, snack bars, fruit leather, health bars, granola, smoothies, soups, juices, cakes, pies, shakes, ice cream, and health drinks.

* * * * *